US010741285B2

(12) United States Patent
Moturu et al.

(10) Patent No.: US 10,741,285 B2
(45) Date of Patent: Aug. 11, 2020

(54) METHOD AND SYSTEM FOR PROVIDING AUTOMATED CONVERSATIONS

(71) Applicant: Ginger.io, Inc., San Francisco, CA (US)

(72) Inventors: Sai Moturu, San Francisco, CA (US); Anmol Madan, San Francisco, CA (US); Greg Elliott, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 716 days.

(21) Appl. No.: 15/482,995

(22) Filed: Apr. 10, 2017

(65) Prior Publication Data

US 2017/0213007 A1 Jul. 27, 2017

Related U.S. Application Data

(63) Continuation-in-part of application No. 13/969,349, filed on Aug. 16, 2013, now Pat. No. 9,836,581.
(Continued)

(51) Int. Cl.
*G16H 40/63* (2018.01)
*G06F 19/00* (2018.01)
(Continued)

(52) U.S. Cl.
CPC ............ *G16H 40/63* (2018.01); *G06F 19/00* (2013.01); *G06F 19/3418* (2013.01);
(Continued)

(58) Field of Classification Search
None
See application file for complete search history.

(56) References Cited

U.S. PATENT DOCUMENTS 96,634 A 11/1869 Thomas
6,356,940 B1 3/2002 Short
(Continued)

FOREIGN PATENT DOCUMENTS

CN 101600008 12/2009
JP 2003339674 12/2003
(Continued)

OTHER PUBLICATIONS

"European Office Action application No. 13 829 654.6, dated Jun. 11, 2019."
(Continued)

*Primary Examiner* — Michael Tomaszewski
(74) *Attorney, Agent, or Firm* — Jeffrey Schox; Caitlin Ploch

(57) ABSTRACT

Embodiments of a method and system for facilitating improvement of a user condition through tailored communication with a user can include receiving a log of use dataset associated with a digital communication behavior at a mobile device, the log of use dataset further associated with a time period; receiving a mobility supplementary dataset corresponding to a mobility-related sensor of the mobile device, the mobility supplementary dataset associated with the time period; determining a tailored communication plan for the user based on at least one of the log of use dataset and the mobility supplementary dataset; transmitting, based on the tailored communication plan, a communication to the user at the mobile device; and promoting a therapeutic intervention to the user in association with transmitting the communication.

20 Claims, 8 Drawing Sheets

Related U.S. Application Data

(60) Provisional application No. 61/683,867, filed on Aug. 16, 2012, provisional application No. 61/683,869, filed on Aug. 16, 2012, provisional application No. 62/320,794, filed on Apr. 11, 2016.

(51) Int. Cl.
  *G16H 10/60* (2018.01)
  *G16H 40/20* (2018.01)
  *G16H 80/00* (2018.01)
  *G16H 20/10* (2018.01)
  *G16H 10/20* (2018.01)

(52) U.S. Cl.
  CPC ......... *G06F 19/3456* (2013.01); *G16H 10/60* (2018.01); *G16H 20/10* (2018.01); *G16H 40/20* (2018.01); *G16H 80/00* (2018.01); *G16H 10/20* (2018.01)

(56) References Cited

U.S. PATENT DOCUMENTS

| | | |
|---|---|---|
| 7,188,151 B2 | 3/2007 | Kumar et al. |
| 7,246,677 B2 | 7/2007 | Fredriksson et al. |
| 7,248,677 B2 | 7/2007 | Randall et al. |
| 7,337,158 B2 | 2/2008 | Fratkina et al. |
| 7,376,700 B1 | 5/2008 | Clark et al. |
| 7,584,166 B2 | 9/2009 | Grichnik |
| 7,761,309 B2 | 7/2010 | Sacco et al. |
| 8,160,901 B2 | 4/2012 | Heywood et al. |
| 8,398,538 B2 | 3/2013 | Dothie et al. |
| 8,500,635 B2 | 8/2013 | Zilca et al. |
| 8,684,922 B2 | 4/2014 | Tran |
| 9,286,442 B2 | 3/2016 | Csoma et al. |
| 9,294,403 B2 | 3/2016 | Mejia et al. |
| 2002/0198473 A1 | 12/2002 | Kumar et al. |
| 2003/0119794 A1 | 6/2003 | Bacaner et al. |
| 2004/0078223 A1 | 4/2004 | Sacco et al. |
| 2004/0225340 A1 | 11/2004 | Evans |
| 2005/0020903 A1 | 1/2005 | Krishnan et al. |
| 2005/0055321 A1 | 3/2005 | Fratkina et al. |
| 2005/0108051 A1 | 5/2005 | Weinstein |
| 2005/0169446 A1 | 8/2005 | Randall et al. |
| 2006/0064037 A1 | 3/2006 | Shalon et al. |
| 2007/0094048 A1 | 4/2007 | Grichnik |
| 2007/0226012 A1 | 9/2007 | Salgado et al. |
| 2007/0288266 A1 | 12/2007 | Sysko et al. |
| 2008/0059570 A1 | 3/2008 | Bill |
| 2009/0125333 A1 | 5/2009 | Heywood et al. |
| 2010/0082367 A1 | 4/2010 | Hains et al. |
| 2010/0179833 A1 | 7/2010 | Roizen et al. |
| 2010/0203876 A1 | 8/2010 | Krishnaswamy |
| 2010/0280838 A1 | 11/2010 | Bosworth et al. |
| 2011/0009715 A1 | 1/2011 | O' Reilly et al. |
| 2011/0066036 A1 | 3/2011 | Zilca et al. |
| 2011/0118555 A1* | 5/2011 | Dhumne .............. A61B 5/16 600/300 |
| 2011/0119212 A1 | 5/2011 | De et al. |
| 2011/0184250 A1 | 7/2011 | Schmidt et al. |
| 2012/0053425 A1 | 3/2012 | Michelson et al. |
| 2012/0143013 A1 | 6/2012 | Davis, III et al. |
| 2012/0221357 A1 | 8/2012 | Krause et al. |
| 2012/0289791 A1 | 11/2012 | Jain et al. |
| 2013/0004129 A1 | 1/2013 | Zhang |
| 2013/0042116 A1 | 2/2013 | Sakumoto |
| 2013/0085758 A1 | 4/2013 | Csoma et al. |
| 2013/0095459 A1 | 4/2013 | Tran |
| 2013/0117040 A1 | 5/2013 | James et al. |
| 2013/0154838 A1 | 6/2013 | Alameh et al. |
| 2013/0179178 A1 | 7/2013 | Vemireddy et al. |
| 2013/0246330 A1 | 9/2013 | Son et al. |
| 2013/0297536 A1* | 11/2013 | Almosni .............. G16H 50/20 706/12 |
| 2014/0039914 A1 | 2/2014 | Dansereau et al. |
| 2016/0317781 A1 | 11/2016 | Proud |

FOREIGN PATENT DOCUMENTS

| | | |
|---|---|---|
| JP | 2010514497 A | 5/2010 |
| JP | 2015514497 A | 5/2015 |
| WO | 085308 | 7/2008 |
| WO | 096634 | 8/2008 |
| WO | 025622 | 3/2012 |
| WO | 042116 | 3/2013 |

OTHER PUBLICATIONS

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

"Major Virginia Smith; et al. 'Work Time Interference With Family, and Psychological Distress' 2002, Journal of Applied Psychology, vol. 87, No. 3, 427-436 (Year: 2002)", Jan. 11, 2018 00:00:00.0.

\* cited by examiner

METHOD AND SYSTEM FOR PROVIDING AUTOMATED CONVERSATIONS

CROSS-REFERENCE TO RELATED APPLICATIONS

This application is a continuation-in-part of U.S. application Ser. No. 13/969,349 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application additionally claims the benefit of U.S. Provisional Application No. 62/320,794 filed 11 Apr. 2016, which is incorporated in its entirety by this reference.

TECHNICAL FIELD

This invention relates generally to the field of healthcare and more specifically to a new and useful method and system for automating user-provider communications in healthcare.

DESCRIPTION OF THE EMBODIMENTS

Figure 1:
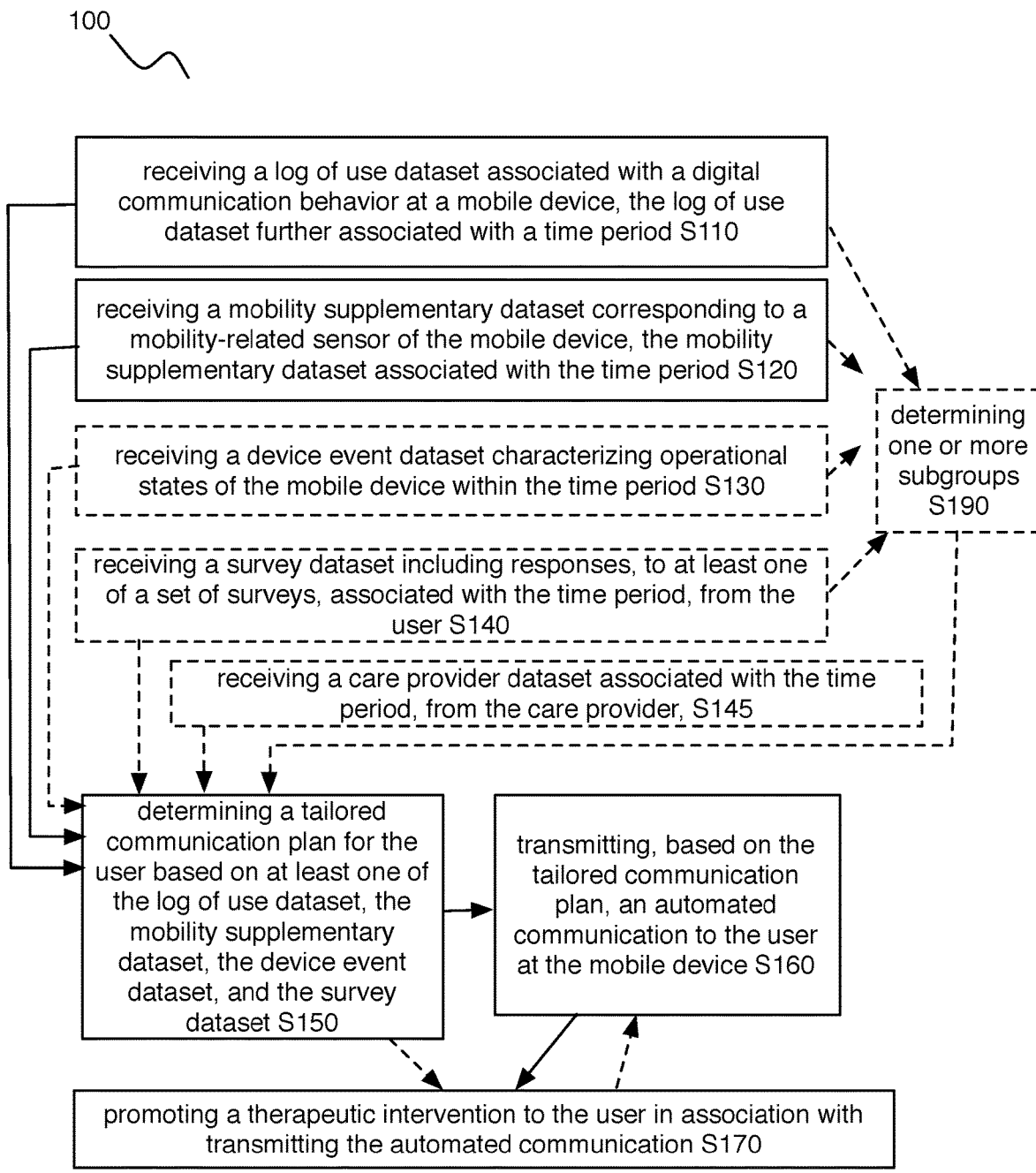
FIGS. 1-2 are flow chart representations of embodiments of a method.
Figure 2:
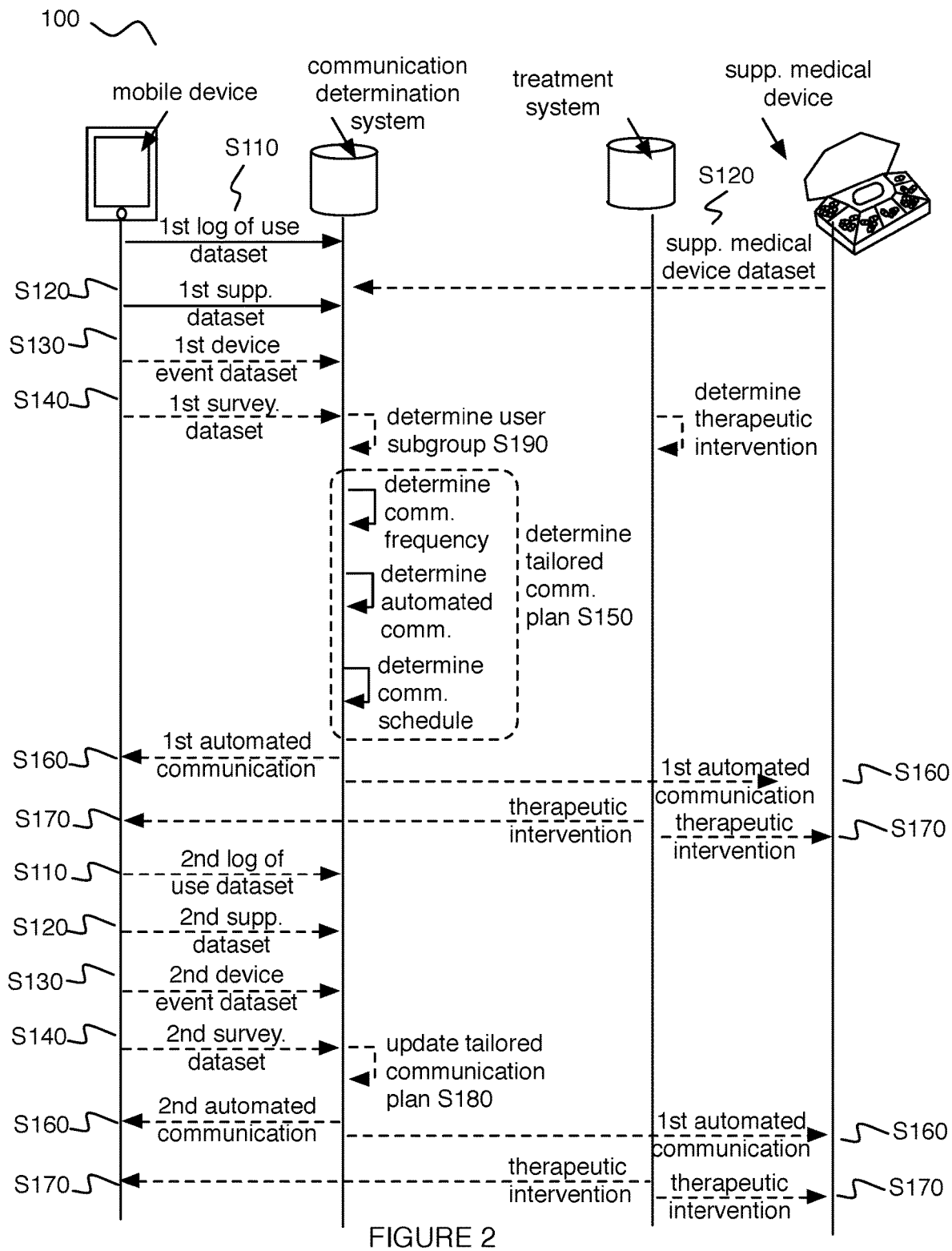

The following description of the embodiments of the invention is not intended to limit the invention to these embodiments, but rather to enable any person skilled in the art to make and use this invention.

1. Overview.

As shown in FIGS. 1-5, embodiments of a method 100 for facilitating improvement of a user condition through tailored communication with a user can include: receiving a log of use dataset associated with a digital communication behavior at a mobile device, the log of use dataset further associated with a time period S110; receiving a mobility supplementary dataset corresponding to a mobility-related sensor of the mobile device, the mobility supplementary dataset associated with the time period S120; determining a tailored communication plan for the user based on at least one of the log of use dataset and the mobility supplementary dataset S150; transmitting, based on the tailored communication plan, a communication to the user at the mobile device S160; and promoting a therapeutic intervention to the user in association with transmitting the communication S170. In variations, determining the tailored communication plan S150, transmitting the communication to the user S160, promoting the therapeutic intervention S170, and/or other portions of the method 100 can be performed automatically with the communication determination system (e.g., generating and transmitting automated communications, etc.), performed and/or facilitated by a care provider (e.g., verifying and/or modifying a tailored communication plan, an automated communication, therapeutic intervention, etc.) and/or by any suitable entity (e.g., non human entity). The method 100 can additionally or alternatively include: receiving a device event dataset characterizing operational states of the mobile communication device within the time period S130; receiving a survey dataset including responses, to at least one of a set of surveys, associated with the time period, from the user S140; receiving a care provider dataset associated with the time period, from the care provider, S145; updating the tailored communication plan for the user based on at least one of a log of use dataset and a mobility supplementary dataset S180; determining one or more user subgroups S190; and/or any other suitable operations.

The method 100 and/or system 200 function to analyze mobile device states, communication behavior, mobility behavior, and/or other information regarding a user (e.g., patient, at-risk user), in order to generate a communication plan personalized to the user and their behaviors over time. In a specific application, the method 100 and/or system 200 can generate tailored communication plans for supporting care providers (e.g., through automated communications that can substitute for manual communication by the care provider; through providing recommended communications for the care provider to transmit to users; etc.) in their interactions with users. In another specific application, the method 100 and/or system 200 can monitor data and behavior detected over to promote therapeutic interventions (e.g., treatments) to the user in association with transmitting automated communications operable to facilitate the promotion of the therapeutic intervention to improve a user condition.

As such, variations of the method 100 and/or system 200 can be implemented in characterizing and/or improving user conditions including any one or more of: psychiatric and behavioral disorders (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); a cardiovascular-related condition (e.g., coronary artery disease; high blood pressure; etc.); rheumatoid-related conditions (e.g., arthritis, etc.); pain-related conditions; endocrine-related conditions; genetic-related conditions; and/or any other suitable type of conditions. Applications of the method 100 and/or system 200 can include characterizing user conditions based on automated communications and/or associated user responses. Information derived from a user population and/or subgroup (e.g., for users communicating with a particular care provider; for users suffering from a particular user condition; etc.) can be used to provide additional insight into user-provider communication behavior (e.g., in relation to a user-provider relationship between a user and a care provider), due to aggregation of data from a population and/or subgroup.

The method 100 is preferably implemented at least in part by an embodiment of the system 200 described in Section 4 below, but can additionally or alternatively be implemented at any suitable components. Additionally or alternatively, one or more instances of the method 100 and/or processes described herein can be performed asynchronously (e.g., sequentially), concurrently (e.g., in parallel; concurrently on different threads for parallel computing to improve system processing ability for performing Blocks of the method 100; etc.), in temporal relation to a trigger event, and/or in any other suitable order at any suitable time and frequency by and/or using one or more instances of the system 200, elements, and/or entities described herein. However, the method 100 and/or system 200 can be configured in any suitable manner.

2. Benefits.

The technology can overcome several challenges faced by conventional approaches for improving patient engagement and/or for supporting care providers. First, conventional approaches can fail to account for the unique communication, mobility, device usage, and/or other behaviors of users, which can be affected by the types of user conditions afflicting different users. Second, conventional approaches can fail to account for the unique communication behaviors and/or manners of promoting therapeutic interventions of care providers, which can lead to impersonal care provider support, impersonal interactions with users (e.g., where a user notices that they are interfacing with an automated system), and/or other ineffectiveness and/or inefficiency. Third, conventional approaches can fail to adapt to changing behaviors of user and care providers over time during the course of a user-provider relationship. Fourth, conventional approaches can fail to account for behaviors in natural settings (e.g., in settings associated with users' daily activities rather than laboratory settings, which the technology can additionally or alternatively take into account). Examples of the method 100 and/or system 200 can confer technologically-rooted solutions to at least the challenges described above.

First, the technology can confer improvements in computer-related technology (e.g., digital communication behavior analytics, tailored automated communication, digital communication support for care provider digital communications with a user, artificial intelligence, digital administration of therapeutic interventions in association with tailored digital communications; etc.) by facilitating computer performance of functions not previously performable. For example, the technology can improve tailoring of communication plans (e.g., live and automated communication with users) and associated promotion of therapeutic interventions through leveraging passively collected digital communication data (e.g., text messaging features, phone calling features, user-provider relationship features, etc.) and/or supplementary data (e.g., mobility behavior data extracted from GPS sensors of mobile devices) that would not exist but for advances in mobile devices (e.g., smartphones) and associated digital communication protocols (e.g., WiFi-based phone calling; video conferencing for digital telemedicine; etc.). As such, the technology can, in examples, unobtrusively and naturally communicate with a user and promote associated therapeutic interventions by continuously gathering a plethora of data that can be used to personalize interactions and treatment delivery for a user and associated changes in behavior over time (e.g., through updating tailored communication plans), while requiring a minimal or otherwise reduced amount of effort by a patient. In a specific example, the technology can enable data collection for users in natural settings (e.g., collecting digital communication behavior data for communications between a care provider and a user in their home), which can enable extraction of insights into a user-provider relationship and associated communications due to natural conditions (e.g., how a user digital communication behavior is affected by daily activities, by interactions with family and friends, etc.).

Second, the technology can confer improvements in computer-related technology through an inventive distribution of functionality across a network including a communication determination system (e.g., a remote computing system receiving and analyzing digital communication data across a plurality of users), a plurality of mobile devices (e.g., associated with users possessing a diversity of communication behaviors, user-provider relationships, user conditions, and/or other suitable characteristics changing over time), a treatment system (e.g., operable to promote one or more therapeutic interventions to the users, such as at the plurality of mobile devices, in association with transmitting communications according to tailored communication plans), and/or other suitable components. For example, the communication determination system can include functionality of analyzing digital communication data previously unused for generating tailored communication plans, such as digital communication data for communications with both care providers and non-care providers; digital communication data in relation to mobility behavior data (e.g., locations at which digital communications were transmitted and/or received; etc.); digital communication data derived from a population of users (e.g., patients) with varying conditions; etc. Such data can be used in providing, evaluating, and/or subsequently updating therapeutic interventions in association with executing transmitting communications according to a tailored, dynamically modifiable communication plan, the personalization of which can improve user engagement (e.g., through improved user experience, ease of use associated with therapeutic interventions and/or a related application executing on the mobile device, etc.) and facilitate therapeutic intervention provision. As such, the technology can provide a centralized, full-stack approach to digitally monitoring, engaging, and treating a patient, leading to improved effectiveness and/or efficiency of care delivery, cost savings, and care delivery scalability.

Third, the technology can confer improvements in computer-related technology through computer-implemented rules (e.g., feature engineering rules; user preference rules; etc.). The increasing prevalence of user digital communication across a plurality of communication protocols and technologies can translate into a plethora of digital communication data (e.g., for both users and care providers), supplementary data (e.g., mobility data), device event data, survey data, and/or other types of data, giving rise to questions of how to process and analyze the vast array of data, such as for automating personalized communication (e.g., in relation to promoting therapeutic interventions) while maintaining a health user-provider relationship. However, the technology can address such challenges by, for example, applying feature engineering rules in generating features (e.g., mobility-communication features associated with digital communication behavior and mobility behavior, such as in relation to user-provider communications) operable to improve processing speed, accuracy, and/or personalization associated with communication plans and/or associated therapeutic interventions (e.g., to enable real-time analysis and response to user communications and needs).

Fourth, the technology can improve the technical fields of at least digital communication, computational modeling of user and/or care provider behavior, digital medicine, and/or other relevant fields. The technology can continuously collect and utilize specialized datasets unique to internet-enabled, non-generalized mobile devices in order to personalize and automate communications between a user and care provider for facilitating treatment. Further, the technology can take advantage of such datasets to better improve the understanding of correlations between user conditions and communications between a user and care provider (e.g., which can include automated communications).

Fifth, the technology can transform entities (e.g., mobile devices, treatment system including medical devices, users, care providers etc.) into different states or things. For example, the technology can automatically initiate provision of therapeutic interventions to the user in association with transmitting communications according to the tailored communication plan to a user mobile device, thereby transforming the user mobile device. In a specific example, the technology can activate an application executing on a smart phone by transmitting an automated communication detailing treatment instructions (e.g., using language and tone tailored for the user) while activating and/or controlling one or more treatment systems (e.g., supplementary medical devices; mobile devices for communication; etc.). In another example, the technology can provide support to care providers by guiding care providers through communications tailored to engage a user, such as through providing recommended communications (e.g., recommended communication content, recommended communication schedule, etc.), insights into user communication behaviors and/or conditions with the user, and/or other suitable digital support, thereby transforming the care provider and the associated care provider mobile devices used in communications with the user. In another example, the technology can determine and/or update therapeutic interventions to promote to a patient in improving user conditions, thereby transforming the user condition and the health of the user. In another example, the technology can transform an audio-enabled personal assistant device, such as operating the personal assistant device to emit automated communications and/or other communications associated with a tailored communication plan.

Sixth, the technology can provide technical solutions necessarily rooted in computer technology (e.g., utilizing computational models for modeling user behavior and/or care provider behavior; dynamically generating and modifying digital, tailored communication plans associated with therapeutic interventions based on the models, and tailored to different user accounts and/or care provider accounts; modifying visually perceptible digital elements corresponding to automated communications to improve, for example, personalization of the automated communications for different users and/or user conditions, etc.) to overcome issues specifically arising with computer technology (e.g., user engagement in the context of digital healthcare; communication personalization to digital communication behaviors, mobile device event behaviors, and associated mobility behavior; modifying elements associated with user interfaces of computer technology to improve user engagement and/or provision of therapeutic interventions).

Seventh, the technology can leverage specialized computing devices (e.g., mobile devices with mobility-related sensors, care provider devices, physical activity monitoring capabilities, digital communication behavior-monitoring capabilities, supplemental medical devices) in automating tailored communication with users. The technology can, however, provide any other suitable benefit(s) in the context of using non-generalized computer systems for improving patient engagement and/or for supporting care providers.

3.1 Method—Receiving a Log of Use Dataset.

Block S110 recites: receiving a log of use dataset corresponding to user digital communication behavior at a mobile device (e.g., mobile communication device), the log of use dataset associated with a first time period. Block S110 functions to unobtrusively collect and/or retrieve communication-related data from a user's mobile device. The log of use dataset preferably includes a log of use of a communication application (e.g., native communication application, phone calling application, messaging application, social media application, etc.) executing on a mobile device of the user within a time period (e.g., a time period associated with a user-provider communication; associated with an automated communication and/or user response; etc.), but can additionally or alternatively include logs of use (e.g., user inputs such as taps, swipes, key presses, etc.) of any suitable application.

The log of use preferably includes one or more communications (e.g., digital communications) between the user and another entity. Communications can include one or more of: user-provider communications (e.g., a care professional communication between one or more users and one or more care providers; a manual communication generated by the care provider; an automated communication generated by the communication determination system and selected by the care provider; etc.), automated communications (e.g., automatically generated and/or transmitted by a communication determination system); associated user responses (e.g., to automated communications; to therapeutic interventions promoted in association with a transmitted communication; etc.); communications between users and non-care providers; and/or any other suitable types of communications. Communications from the log of use are preferably associated with one or more time periods (e.g., during, before, and/or after the communication was transmitted). The time period can include a time duration (e.g., seconds, minutes, hours, days, etc.), an absolute time (e.g., indicated by a timestamp), be specific to a user (e.g., a time period associated with a user's daily activity), be specific to a user condition (e.g., a time period associated with measuring blood glucose level for diabetics), be specific to a care provider (e.g., a time period associated with care provider operating hours), and/or can include any suitable type of temporal indicator. For example, a log of use can be associated with a time period within which an automated communication was transmitted, an associated therapeutic intervention was promoted, and a user response (e.g., survey response; text message; etc.) was received. However, communications and associated time periods can be configured in any suitable manner.

Preferably, Block S110 is implemented using a module of a processing subsystem configured to interface with a native data collection application executing on a mobile device (e.g., smartphone, tablet, personal data assistant, personal music player, vehicle, head-mounted wearable computing device, wrist-mounted wearable computing device, etc.) of the user. As such, in one variation, a native data collection application can be installed on the mobile device of the user, can execute substantially continuously while the mobile device is in an active state (e.g., in use, in an on-state, in a sleep state, etc.), and can record communication parameters (e.g., communication times, durations, contact entities) of each inbound and/or outbound communication from the mobile device. In implementing Block S110, the mobile device can then upload this data to a database (e.g., remote server, cloud computing system, storage module), at a desired frequency (e.g., in near real-time during a communication, after communications, before communications, every hour, at the end of each day, etc.) to be accessed by the processing subsystem. For example, Block S110 can include, in response to transmitting an automated communication to a mobile device associated with the user, logging digital communications (e.g., time, frequency, content, participants, application, etc.) into a log of use for a time period (e.g., for an hour following transmitting the automated communication; until the user fails to respond for a threshold amount of time; continuously; etc.); and streaming the corresponding log entries to a remote communication determination system in substantially real-time (e.g., where the log of use can be subsequently processed in other Blocks of the method 100).

As such, Block S110 preferably enables collection of one or more of: phone call-related data (e.g., number of sent and/or received calls, call duration, call start and/or end time, location of the user before, during, and/or after a call, and number of and time points of missed or ignored calls); text messaging (e.g., SMS text messaging) data (e.g., number of messages sent and/or received, message length associated with a contact of the user, message entry speed, delay between message completion time point and sending time point, message efficiency, message accuracy, time of sent and/or received messages, location of the user when receiving and/or sending a message, media such as images, charts and graphs, audio, video, file, links, emojis, clipart, etc.); data on textual messages sent through other communication venues (e.g., public and/or private textual messages sent to contacts of the user through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments; textual and/or audio inputs collected from a user in response to automated textual and/or voice communications; etc.) and/or any other suitable type of data. However, collecting a log of use dataset S110 can be performed in any suitable manner.

3.2 Method—Receiving a Supplementary Dataset.

Block S120 recites: receiving a supplementary dataset characterizing activity of the user in association with the time period, which functions to unobtrusively receive non-communication-related data from a user's mobile device and/or other device configured to receive contextual data from the user. Block S120 can include receiving non-communication-related data pertaining to the user before, during, and/or after (or in the absence of) communication with another entity (e.g., care provider; communication determination system; non-care provider etc.) and/or computer network (e.g., a social networking application), as described above in relation to Block S110. For example, block S120 can include collecting a mobility supplementary dataset indicating each of the locations at which a user received an automated communication and/or care provider communication, and/or at which a user transmitted a communication to a care provider and/or communication determination system. In another example, Block S120 can include receiving a mobility supplementary dataset indicating locations at which therapeutic interventions were promoted to the user in association with communications corresponding to a tailored communication plan. Block S120 can additionally or alternatively include receiving data associated with user activity from one or more application programming interfaces (APIs) configured to provide user-specific activity information (e.g., a Google API for user activity, an Apple Health Kit API, etc.).

In some variations, Block S120 can include receiving one or more of: location information, movement information (e.g., related to physical isolation, related to lethargy), device usage information (e.g., screen usage information, physical movement of the mobile device, etc.), device authentication information (e.g., information associated with authenticated unlocking of the mobile device), and/or any other suitable information. For instance, the supplementary dataset can include a mobility supplementary dataset including a log of times when the user has picked up and/or placed the mobile device down, in able to determine when the mobile device was in use. Such data can be used to flag certain time periods as time periods where the user was awake. In variations, Block S120 can include receiving a mobility supplementary dataset including location information of the user by way of one or more of: receiving a GPS location of the user (e.g., from a GPS sensor within the mobile device of the user), estimating the location of the user through triangulation of local cellular towers in communication with the mobile device, identifying a geo-located local Wi-Fi hotspot during a phone call, and in any other suitable manner. In specific examples, Block S120 can include collecting a mobility supplementary dataset including one or more of: user location data (e.g., a user located inside their private house when communicating with a care provider as opposed to a public location, etc.), physical activity data (e.g., footstep parameters; heart rate above a threshold amount exceeding an average resting heart rate while communicating with a care provider and/or communication determination system; accelerometer and/or gyroscope data; breathing patterns; other cardiovascular and/or physical activity parameters; etc.), and/or any other suitable data. In applications, data received in Block S110 and S120 can be processed to track behavior characteristics of the user, such as mobility, periods of isolation, quality of life (e.g., work-life balance based on time spent at specific locations), and any other location-derived behavior information.

In some variations, Block S120 can include collecting biometric data associated with user conditions, such as from electronic health records, sensors of mobile devices and/or supplemental medical devices, user inputs (e.g., entries by the user at the mobile device), and/or other suitable sources. Biometric data can include one or more of: electroencephalogram (EEG) data, electrooculogram (EOG) data, electromyogram (EMG) data, electrocardiogram (ECG) data, airflow data (e.g., nasal airflow, oral airflow, measured by pressure transducers, thermocouples, etc.), pulse oximetry data, sound probes, polysomnography data, family conditions, genetic data, microbiome data, and/or any other biometric data.

Furthermore, variations of Blocks S110, S120, and/or other portions of the method 100 can be implemented in manners analogous to those described in U.S. application Ser. No. 15/005,923 entitled "Method for Providing Therapy to an Individual" and filed on 25 Jan. 2016, which is incorporated in its entirety by this reference. Variations of the method 100 can, however, omit any portion of the method 100 in determining communication plans S150, promoting therapeutic interventions in association with communication plans S160, and/or performing nay portions of the method 100. However, collecting supplementary datasets can be performed in any suitable manner.

3.3 Method—Receiving a Device Event Dataset.

Some variations of the method 100 can additionally or alternatively include Block S130, which recites: receiving a device event dataset characterizing operational states of the mobile device within the time period. Block S130 functions to provide device event data as an input for other suitable portions of the method 100. The device event dataset can include data associated with changes in states of the device, such that a change in device state triggers transmission of device event data to the communication determination system in Block S130. Additionally or alternatively, the device event dataset can be associated with sampling (e.g., regular sampling, intermittent sampling, random sampling, etc.) of device event information stored in a log at the mobile device, such that Block S130 includes receiving a dataset including a set of time points and one or more aspects of device state at each of the set of time points. In a specific example, sampling of a log of device events of the mobile device can be performed at a sub-minute frequency; however, in variations of the specific example, the log can be sampled at any other suitable frequency.

In variations of Block S130, the device event data can provide time points of device events associated with one or more of: device charging (e.g., the device has transitioned to or from a charging state; etc.), device powering (e.g., the device has transitioned between a powered off state and a powered on state; etc.), device idling (e.g., the device has transitioned between an active state and an idling state; etc.), intelligent personal assistant activation (e.g., activation of Apple Siri, activation of Google Now, activation of Windows Cortana, activation of Amazon Echo, etc.), intelligent personal assistant inputs (e.g., audio inputs spoken by the user to the intelligent personal assistant), alarm clock states (e.g., alarm clock on state, alarm clock off state, alarm clock snoozing state, etc.), audio output device state (e.g., music application activity state), video output device state (e.g., video application activity state), media casting state (e.g., music/video being cast to other devices, such as Chromecast, Miracast, Airplay devices, etc.), sensor activation state (e.g., initiation and/or cessation of sampling of sensor measurements, types of sensors activated, etc.), communicative state (e.g., connectivity, transmission, receiving, etc.), Bluetooth connectivity state in relation to other devices (e.g., a wireless alarm clock), and/or any other suitable device event. Additionally or alternatively, the device event data can include data from sensors (e.g., accelerometer, gyroscope, other motion sensors, other biometric sensors, etc.) implemented with the mobile device and/or other suitable devices, as described in U.S. application Ser. No. 13/969, 339 entitled "Method for Modeling Behavior and Health Changes" and filed on 16 Aug. 2013. However, collecting device event datasets S130 can be performed in any suitable manner.

3.4 Method—Receiving a Survey Dataset.

Some variations of the method 100 can additionally or alternatively include Block S140, which recites: receiving a survey dataset (e.g., included in a supplementary dataset) including responses, to at least one of a set of surveys, associated with a set the time period (e.g., including a set of time points), from the user, care provider, and/or other suitable entity. Block S140 can function to provide survey data associated with a specific time period in the life of the user and/or associated users (e.g., care provider, family, friend, etc.). Block S140 can additionally or alternatively be used to aggregate survey data from the user over time, in order to generate a personalized model of the user's behavior (e.g., digital communication behavior) from self-reported data. Block S140 can additionally or alternatively be used to aggregate survey data from a population (e.g., subgroup) of users, in order to generate a population model of behavior for a population of users. As such, personalized and/or population-wide models can be used to inform assessments of digital communication behaviors (e.g., in relation to a care providers) for each of a population of users and/or associated users. The survey dataset can include interview and/or self-reported information. Furthermore, the survey dataset preferably includes quantitative data, but can additionally or alternatively include qualitative data pertaining to a user condition of the user. Furthermore, while portions of the survey dataset preferably correspond to time points within the time period of Block S110, portions of the survey dataset can alternatively correspond to time points outside of the time period of Block S110 (e.g., as in a pre-screening or a post-screening survey; pre-therapeutic intervention or post-therapeutic intervention). Additionally or alternatively, Block S140 can include receiving clinical data (e.g., information gathered in a clinic or laboratory setting by a clinician) and/or any other suitable data.

In variations, associated time periods can include regularly-spaced time points (e.g., time points spaced apart by an hour, by a day, by a week, by a month, etc.) with a suitable resolution for enabling detection of transitions between states of the user. Additionally or alternatively, provision of a survey and/or reception of responses to a survey can be triggered upon detection of an event of the user (e.g., based upon data from sensors associated with the user, based upon an output of an analysis of subsequent blocks of the method 100, etc.) and/or any other suitable change in state of the user. Furthermore, for all time points of the time period, an identical subset of the set of surveys can be provided to the user; however, in alternative variations, different subsets of the set of surveys can be provided to the user at different time points of the set of time points.

In variations of Block S140, the survey dataset can include responses to surveys configured to assess or validate user engagement, user-provider relationships, degree of personalization, condition-related parameters (e.g., sleep-related parameters; cardiovascular-related parameters; etc.) associated with a user condition, and/or any other suitable metrics. Additionally or alternatively, Block S140 can be performed to assess or validate aspects analogous to those described in U.S. application Ser. No. 15/005,923 entitled "Method for Providing Therapy to an Individual" and filed on 25 Jan. 2016, and in U.S. application Ser. No. 15/265,454 entitled "Method for Providing Health Therapeutic Interventions to a User" and filed on 14 Sep. 2016, each of which is incorporated in its entirety by this reference. However, collecting a survey dataset S140 can be performed in any suitable manner.

3.5 Method—Receiving a Care Provider Dataset.

Figure 4:
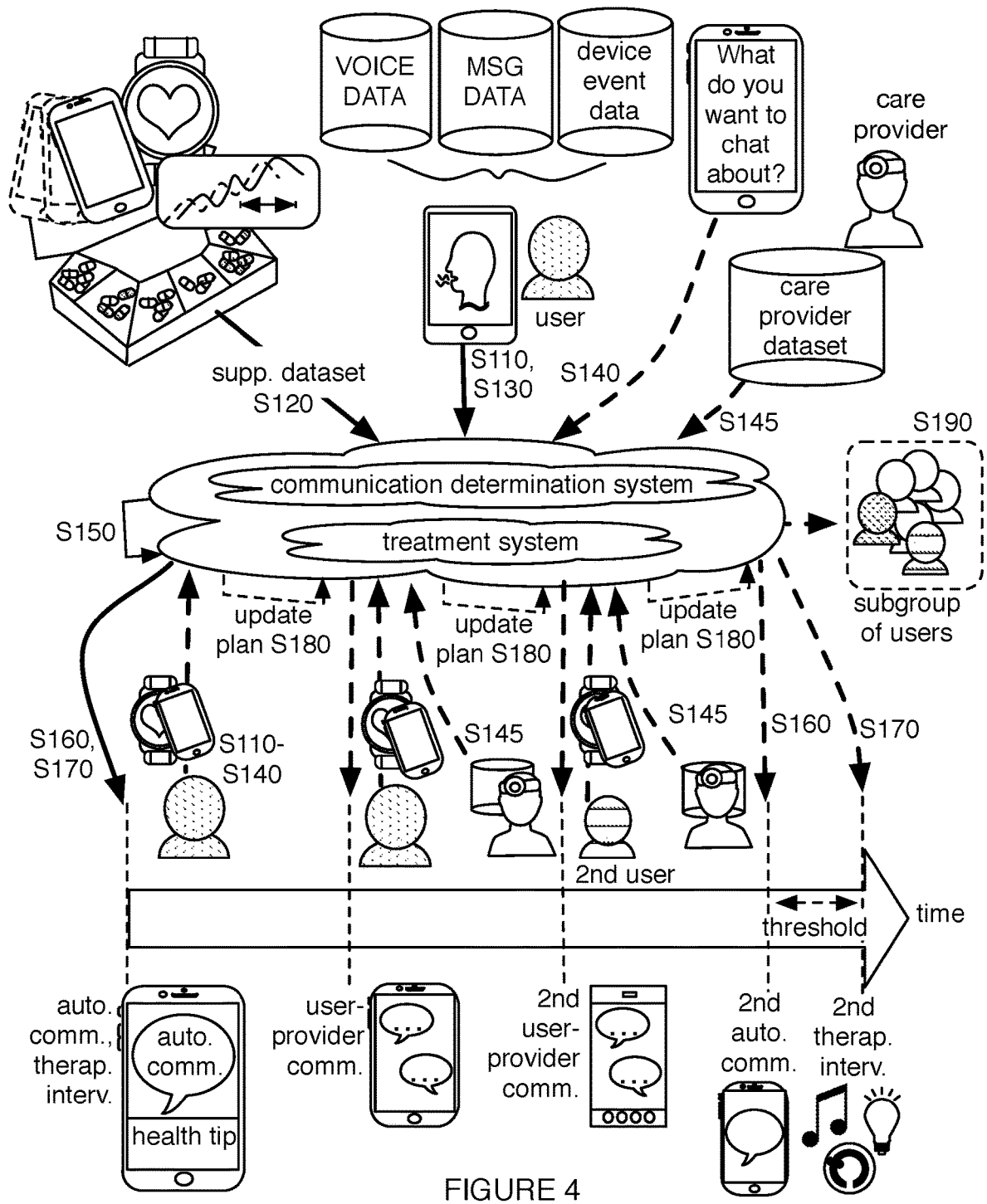
FIG. 4 is a schematic representation of an embodiment of a method.

As shown in FIG. 4, some variations of the method 100 can additionally or alternatively include Block S145, which recites: receiving a care provider dataset in association with a time period, which functions to receive data (e.g., types of data described in Blocks S110-S140, etc.) for use in generating and/or executing a communication plan and/or associated therapeutic interventions, and/or for any other purpose. In relation to Block S145, a care provider can include any one or more of: a health coach, psychiatrist, physician, healthcare professional, therapist, guardian, friend, and/or any suitable provider of care for one or more users. A care provider dataset preferably includes care provider observations, survey responses (e.g., to surveys analogous to those described in Block S140), assessments and/or insights regarding communications (e.g., textual communications, audio, video, automated communications, etc.) with a user, regarding communication plans, regarding therapeutic interventions, and/or any other suitable aspects, but can include any suitable data in relation to one or more users. User-provider communications can be through any one or more of: in-person communication (e.g., a scheduled appointment), digital communication (e.g., text messaging communication), and/or any suitable venue.

For Block S145, care provider data can be collected through a web interface, an application executing on a mobile device (e.g., a care provider device), and/or any suitable venue. For example, Block S145 can include receiving a care provider dataset in response to prompting a care provider to provide a care provider input (e.g., at a web interface displaying user information including a user improvement evaluation, etc.), such as after completion of a user-provider communication. Care provider data is preferably collected, processed, and/or leveraged for the generation and administration of a tailored communication plan. For example, the method 100 can include receiving a first care provider dataset during a first time period; generating a tailored communication plan based on the first care provider dataset; receiving a second care provider dataset during a second time period subsequent the first time period; and dynamically updating the tailored communication plan based on the second care provider dataset. However, collecting and/or leveraging a care provider dataset can be performed at any suitable time. Additionally or alternatively, receiving a care provider dataset can be performed in any manner analogous to embodiments, variations, and examples described in U.S. application Ser. No. 15/005,923, entitled "Method for Providing Therapy to an Individual" and filed on 25 Jan. 2016, which is herein incorporated in its entirety by this reference. However, Block S145 can be performed in any suitable manner.

Blocks S110-S145 can thus provide passive data (e.g., unobtrusively collected data) and/or active data (e.g., survey data) that can be taken as inputs in Block S150 and/or other portions of the method 100 in order to generate communication plans tailored to past, present, and/or future user behaviors, user conditions, care provider behaviors, and/or any other suitable aspects associated with a user-provider relationship. Data in relation to Blocks S110-S145 can be associated with any suitable communications (e.g., automated communications, user-provider communications, etc.), time periods, and/or other suitable components. Blocks S110-S145 can include collecting data at any suitable time in relation to any suitable trigger event (e.g., transmitting and/or receiving of communications; completion of communications; promotion of therapeutic interventions; etc.); however, Blocks S110-S145 can include collecting data in any suitable manner.

3.6 Method—Determining a Communication Plan.

Figure 8:
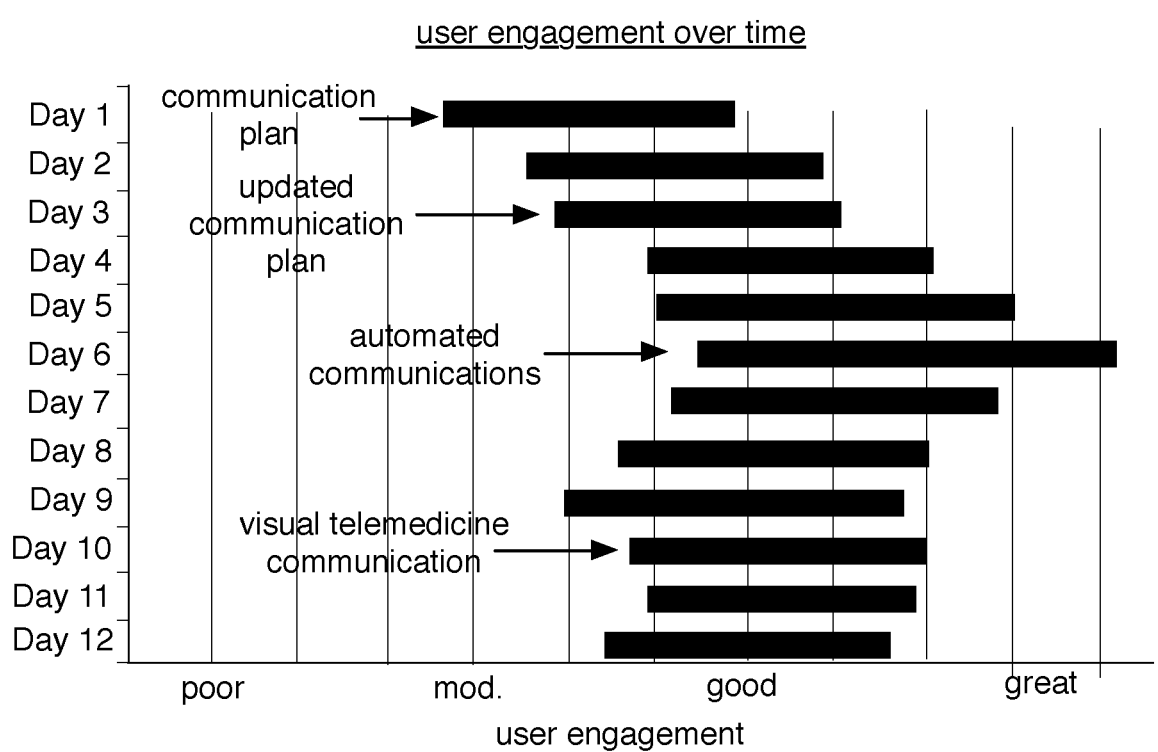
FIG. 8 is a graph of user engagement over time.

Block S150 recites: determining a tailored communication plan for the user based on at least one of the log of use dataset and the mobility supplementary dataset. Block S150 can function to generate a communication plan personalized for guiding interactions with a user in order to support care providers (e.g., in their communications with a user), promote user engagement (e.g., as shown in FIG. 8), facilitate treatment (e.g., with associated therapeutic interventions) to improve a user condition, and/or to achieve any other suitable purpose. For example, executing different tailored communication plans for different users can entail different automated communications delivered to different users despite similar user inputs, but executing different communication plans can alternatively include facilitating similar communications based on similar user inputs.

In relation to Block S150, communication plans are preferably associated with one or more: users (and/or associated users, such as family, friends, individuals sharing a subgroup with the user, etc.) (e.g., associating a communication plan with a user identifier identifying the user at a database of the communication determination system), care providers (e.g., associating communication plans with care provider identifiers at the database), user conditions (e.g., associating user conditions with communication plans tailored to the user condition based on the effects of the user condition on user communication behavior), user-provider relationships (e.g., associating a communication plan with a pair of identifiers including a user identifier and a care provider identifier), and/or any other suitable aspects. Components of communication plans can be retrieved (e.g., from a database of the communication determination system) at suitable times (e.g., based on communication schedules) for guiding communication and/or therapeutic intervention provision in relation to users and/or associated locations (e.g., delivering an appropriately timed automated communication to a user for re-engaging a user, at a location where the user is historically receptive to receiving digital healthcare-related communications). However, associating and/or retrieving communication plans can be performed in any suitable manner. Generated communication plans are preferably tailored to one or more: users, user conditions, care providers, and/or other suitable aspects, but can alternatively be independent from and/or otherwise related to any suitable entities.

Regarding Block S150, communication plans preferably include one or more automated communications (e.g., a communication automatically generated by the communication determination system; automated communication templates generated and presented to a care provider, who can subsequently modify and/or transmit care provider communications derived from the automated communication templates; etc.). Automated communications can include one or more content components defining types of content expressed in the automated communications. Content components can include any one or more of: engagement communications (e.g., initial proactive outreach to new users; re-engagement outreach to inactive users; reinforcement such as positive reinforcement for users who are cooperating with therapeutic interventions, for users who are actively engaged with a tailored communication plan, for users responding to surveys; negative reinforcement for users who are struggling with medication adherence; etc.); therapeutic intervention-related communications (e.g., therapeutic interventions administered through automated communications, such as health tips; therapeutic intervention communications provided in response to identifying user conditions and/or needs based on the communications; associated instructions; hyperlinks to therapeutic interventions determined based on communications with users; medication-related communications such as reminders, associated dosages, types of medications, associated risks, warnings; etc.); survey-related communications (e.g., survey provision through automated communications, such as through guiding the user through a series of survey questions while dynamically generating analyses of their answers, which can be used to trigger updated automated communications; automated communications surveying aspects about the tailored communication plan; a question regarding user actions and/or behavior; etc.); user condition-related communications (e.g., characterizations of the user conditions; educational information, such as metrics, concerning the user conditions; etc.); application-associated communications (e.g., guiding the user through usage of an application executing on the mobile device, such as an application through which automated communications and care provider communications are presented; troubleshooting and usage tips; introducing new application feature and/or capabilities; etc.); and/or any other suitable types of content. However, content components can be configured in any suitable manner.

Relating to Block S150, automated communications preferably include one or more format components defining format-related aspects associated with presentation of the automated communication. The format components can include any one or more of: user-specific format parameters (e.g., modifications to a content component to express the content component in a manner personalized to the user, such as in relation to language, characters used, associated media, colors, etc.); textual parameters (e.g., text-based communications; font size; font color; font type; other font parameters; spacing parameters; etc.); graphical parameters (e.g., visual-based parameters, communications including images, video, virtual reality, augmented reality, colored blinking light notifications, etc.); other parameters associated with visually perceptible digital elements (e.g., sizing, highlighting, etc.); audio parameters (e.g., audio-based communications such as through music, sound notifications, a human voice, a personal assistant device; volume parameters; tone parameters; pitch parameters; etc.); touch parameters (e.g., braille parameters; haptic feedback parameters; etc.); delivery-related parameters (e.g., recipient device such as mobile device versus smart appliance; communication protocol; etc.) and/or any other format-related parameters. An automated communication can include any suitable type and/or number of format components for a given content component (e.g., different manners of formulating and/or expressing the same content). Additionally or alternatively, automated communications can include any number of content components for a given format component (e.g., a same set of font parameters for expressing different types of content). However, format components can relate to content components in any suitable manner. However, format components of automated communications can be configured in any suitable manner.

Figure 5:
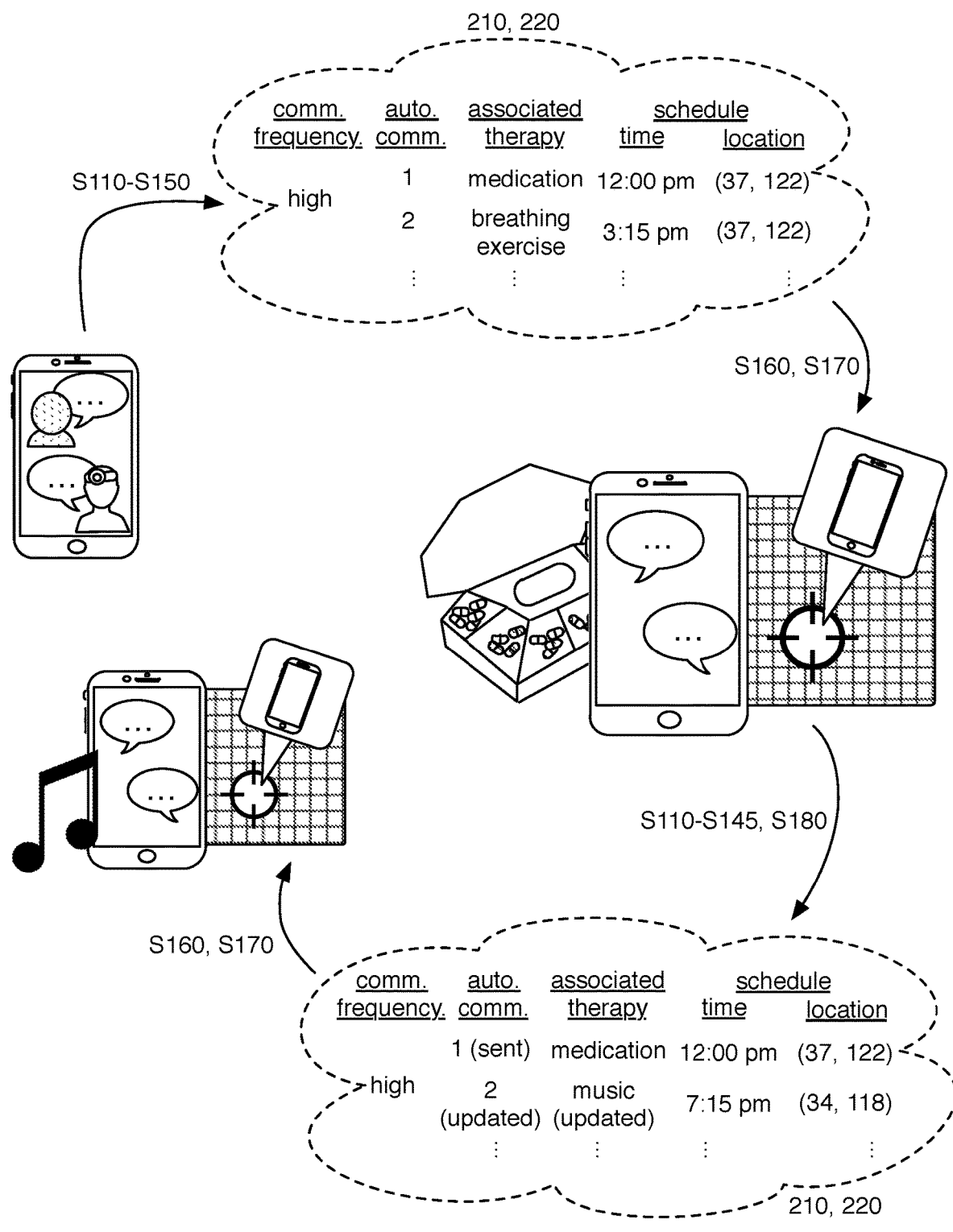
FIG. 5 is a schematic representation of an embodiment of a method.

For Block S150, a communication plan can additionally or alternatively include one or more: communication schedules (e.g., scheduling time, location, trigger events such as a device events, associated with transmitting communications, etc.), communication frequency parameters (e.g., indicating frequency of transmitting communications, such as a low communication frequency corresponding to fewer than one communication a day, a high communication frequency corresponding to three or more communications a day, etc.), care provider match parameters (e.g., for matching one or more users to one or more care providers for developing a user-provider relationship and/or facilitating user-provider communications; for updating a care provider match for a user, such as based on historic user-provider communications between the user and a previously matched care provider; matching the user to a new care provider based on negative user sentiment towards user-provider communications with a previously matched care provider; etc.), and/or any other suitable components. For example, as shown in FIG. 5, a communication schedule can include a target geographical location and/or a target time for transmitting automated communications, associated therapeutic interventions, and/or any other suitable components. In examples, determining communication schedules and/or other components of a communication plan can be based on one or more of: a care provider availability schedule (e.g., indicating time periods of availability for the care provider, indicating scheduled communications between the care provider and a plurality of users, indicating operating hours associated with the care provider, etc.), other care provider parameters (e.g., digital communication behaviors of care providers, care provider personalities, etc.), care provider device parameters (e.g., time period associated with frequent device activity, etc.), user parameters (e.g., medical history, demographics, user personality, time periods associated with high frequency of digital communication), user device parameters (e.g., type of user device), trigger events (e.g., scheduling communications in association with user onboarding; user inactivity; initialization of an application on the mobile device; emergency events such as based on extracting meaning based on communications; transition events for transitioning between a care provider and the automated communication determination system such as based on user sentiment in relation to automated communications etc.), and/or any other suitable parameters. In a specific example, determining a communication schedule can include ranking users of a set of users for communication provision (e.g., scheduling who to reach out to first; prioritizing different incoming users; etc.), and scheduling automated communications and/or care provider communications to be transmitted based on the ranking.

In a variation of Block S150, determining a communication plan (and/or associated components) can be based on historic communications (e.g., historic automated communications, user-provider communications, associated user responses, communications associated with other users such as users sharing a subgroup, etc.). Determining a communication plan based on historic communications can include one or more of, in relation to historic communications: determining contextual parameters (e.g., based on data from Blocks S110-S145, etc.), extracting meaning (e.g., user meaning associated with user inputs), determining sentiment (e.g., emotional sentiment associated with a communication, with a therapeutic intervention, with an application feature, etc.), topic tagging (e.g., detecting, categorizing, and/or otherwise tagging communications with topics, which can be used for determining and/or promoting therapeutic interventions, identifying transition events for transitioning between care providers and an automated communication determination system for transmitting communications, summarizing communications for subsequent analysis, updating communication plans, searching communications, determining content components and/or format components, etc.), summarizing communication content (e.g., for documentation such as in relation to the Health Insure Portability and Accountability Act and/or other regulations; for supporting care providers by providing summaries of historic communications with the user; for topic tagging; etc.), and/or any other suitable processes. In an example relating to user sentiment, Block S150 can include transmitting an automated communication including a content component (e.g., a re-engagement communication); receiving a user response to the automated communication; extracting user sentiment (e.g., using natural language processing algorithms) based on the user response; and modifying the frequency of scheduled automated communications including the content component (e.g., increasing the frequency of re-engagement communications based on a positive emotional user sentiment concerning the re-engagement communication). In another example relating to user sentiment, the method 100 can include: dynamically modifying a series of questions included in a survey based on user sentiment extracted from survey responses to questions from the series of questions (e.g., generating automated communications investigating the reasons for why a user disliked a therapeutic intervention in response to determining a negative emotional sentiment based on survey responses concerning the therapeutic intervention, etc.). In an example relating to digital communication behavior, Block S150 can include generating automated communications including format components selected to emulate care provider communication digital communication behavior (e.g., frequency of digital communications, format of digital communications, etc.) determined based on historic care provider communications. In another example, communications between the user and non-care providers can be used to determine components of a tailored communication plan (e.g., extracting user sentiment towards discussing different topics associated with the user condition; and determining a communication frequency for automated communications associated with the different topics based on the extracted user sentiment; etc.). In another example, Block S150 can include determining an automated communication frequency based on user condition and digital communication behavior in relation to non-care providers (e.g., based on frequency of digital communications with non-care providers). In another example, user-provider communications for a set of other users excluding the user can be used in determining a communication plan for the user (e.g., communications between other users and a care provided matched to the user).

In another variation of Block S150, determining a communication plan can be based on mobility supplementary data. For example, Block S150 can include determining a communication schedule specifying a target geographical location for transmission of automated communications based on a location identified with frequent digital communication behavior from the user (e.g., a location where the user has transmitted the most text messages, etc.). In another example, Block S150 can include scheduling an automated communication based on user physical activity (e.g., for when a user is physically inactive, based on motion sensor data; for after a user exercises, based on motion sensor data, etc.). In another variation of Block S150, determining a communication plan can be based on one or more therapeutic interventions. For example, Block S150 can include generating an automated engagement communication based on user response to promoted therapeutic interventions (e.g., transmitting a re-engagement communication in response to user inactivity following a therapeutic intervention). In another example, Block S150 can include matching a user to a care provider specializing in a type of therapeutic intervention (e.g., cognitive behavior therapy-based interventions) in response to identifying user improvement in relation to the type of therapeutic intervention. In another example, Block S150 can include scheduling automated communications based on identifying user conditions (e.g., based on survey responses) suitable for therapeutic interventions.

In another variation, of Block S150, determining a communication plan can be based on care provider parameters, which can include one or more of: care provider personality (e.g., extracting a care provider personality from historical care provider communications, the personality indicative of care provider digital communication behavior; and modifying automated communication templates based on the care provider personality); care provider specialty (e.g., matching users to care providers based on suitability of care provider specialty to user condition); care provider availability (e.g., scheduling automated communications for time periods associated with care provider unavailability; etc.); and/or any other suitable care provider parameters; In another variation of Block S150, determining a communication plan can be based on user parameters, which can include one or more of: user personality (e.g., openness to digital communication; openness to discussing topics associated with their user condition; tone; user sentiment; etc.); user condition (e.g., assigning a high communication frequency for communicating with a user based on a personality disorder indicating a need for frequent human interaction; assigning a high care provider communication frequency for a user with a high-risk user condition, such as severe depression associated with suicidal behavior; etc.); user goals (e.g., determined based on survey responses); user engagement; and/or other suitable user parameters. In another variation of Block S150, determining a communication plan can be based on third party resources, including one or more of: internet resources (e.g., generating automated communications including hyperlinks to Internet educational resources, to resources associated with therapeutic interventions such as a medication dosage online information, etc.), third party databases (e.g., generating automated communications including content retrieved from API requests to third party databases, such as electronic health record databases, social media databases, other third party databases associated with the user, etc.), and/or any other suitable resources.

Determining a communication plan in Block S150 can additionally or alternatively include determining and/or applying communication-related features. Communication-related features can include any of: textual features (e.g., word frequency, sentiment, punctuation associated with words present in text messages; etc.), graphical features (e.g., emojis and/or other media included in text messages; media posted to social networking sites; media transmitted and/or received through digital messages; associated pixel values; etc.), audio features (e.g., Mel Frequency Cepstral Coefficients extracted from audio inputs captured by the mobile device, such as in response to an automated audio communication emitted by a intelligent personal assistant, etc.), cross-user features (e.g., average frequency of text messages; average length and/or duration of phone calls and/or text messaging; users participating in a digital communication; features across users in a subgroup, etc.), cross-care provider features (e.g., care provider communication features associated with subgroups of care providers, etc.), combinations of feature types, and/or any other suitable feature types. In an example, Block S150 can include extracting, from at least one dataset collected in Blocks S110-S145, a set of features based on one or more computer-implemented rules (e.g., a feature engineering computer-implemented rule operable to improve a communication model); and determining a communication plan based on the set of features. Applying a feature engineering rule can include applying a feature selection rule to filter, rank, and/or otherwise select features for use in determining communication plans. Feature selection rules can select features based on optimizing for personalization to users, processing speed, accuracy, characterization of user conditions, promotion of therapeutic interventions, and/or any other suitable criteria. Choice of feature selection rules can be based on user parameters, care provider parameters, historic communications, and/or any other suitable criteria described in relation to determining an communication plan.

In a variation, Block S150 can include extracting mobility-communication features (e.g., text messaging location features associated with text messaging communication behaviors and mobility behaviors; phone calling features associated with phone calling communication behaviors and mobility behaviors; etc.). In a specific example, Block S150, can include extracting, from the log of use dataset and the mobility supplementary dataset, a set of mobility-communication features associated with the user-provider relationship based on a feature engineering computer-implemented rule. In another specific example, Block S150 can include extracting a set of mobility-communication features including a text messaging location feature based on associating a text messaging parameter from the log of use dataset with a location parameter from the mobility supplementary dataset, according to the feature engineering computer-implemented rule. Text messaging location features include any one or more of, at a location and between the user a care provider: text messaging frequency (e.g., number of text messages transmitted and/or received associated with a time period; timestamps associated with text messages during a time period; etc.), text messaging duration (e.g., a time period associated with a plurality of text messages), text messaging content, and/or any other suitable features. In another specific example, phone calling location features can include any features analogous to text messaging location features. In another variation, Block S150 can include mobility-device event features (e.g., features associated with mobility behavior and a device events, such as application activity at a location, social media activity at a location, etc.). In another variation, Block S150 can include user condition-communication features (e.g., features associated with communications related to the user condition). Additionally or alternatively, any suitable datasets can be processed alone or in combination to generate any suitable types of features. However, determining and/or applying communication-related features can be performed in any suitable manner.

Determining a communication plan in Block S150 can additionally or alternatively include generating and/or applying a communication model. Communication models preferably output one or more components of a communication plan based on communication-related features and/or datasets, but any suitable inputs can be leveraged by communication models for generating any suitable outputs. The communication model can include any one or more of: probabilistic properties, heuristic properties, deterministic properties, and/or any other suitable properties. In a variation, the communication model can include weights assigned to different communication-related features and/or datasets. For example, features extracted from user-provider communications can be weighted more heavily than features extracted from communications between a user and a non-care provider. In another example, mobility behaviors associated with promoted therapeutic interventions (e.g., user locations where a therapeutic intervention is provided) can be weighted more heavily than mobility behaviors associated with user daily activities. In another variation, applying a communication model can include applying a communication decision tree model, such as a decision tree model including internal nodes and branches selected based on correlations between automated communications and user outcomes (e.g., in relation to user conditions). In a specific example, a communication decision tree model can start with an initial automated communication (e.g., to be transmitted to the user), and subsequent automated communications can be selected and transmitted based on user responses (e.g., associated user meaning, user sentiment, etc.) to communications. However, applying communication decision tree models can be performed in any suitable manner.

In another variation of Block S150, applying a communication model can include applying one or more machine learning communication models employing one or more machine learning approaches analogous to those described in U.S. application Ser. No. 15/265,454 entitled "Method for Providing Health Therapeutic Interventions to a User" and filed on 14 Sep. 2016, which is herein incorporated in its entirety by this reference, and/or any other suitable form of machine learning algorithm. In a specific example, the method 100 can include: applying a machine learning communication model to tag a communication with a topic (e.g., where the communication model is trained on a training dataset including text messages and associated topic labels); mapping the topic to a subset of potential automated communications associated with the topic; and selecting an automated communication to transmit to the user from the subset of potential automated communications. In another specific example, Block S150 can include training a neural network model (e.g., a generative neural network model) with an input neural layer using features derived datasets described in Blocks S110-S145 to dynamically output content components for an automated communication, and/or any other suitable components of a communication plan. In specific examples, Block S150 can include training and applying a reinforcement learning model (e.g., deep reinforcement learning model), such as a reinforcement learning model for maximizing a reward (e.g., determining components of a communication plan for optimizing user outcomes, improving user conditions, user openness, and/or other suitable user parameters, etc.); a reinforcement learning model (e.g., inverse reinforcement learning model) for mimicking an observed behavior (e.g., care provider communication behavior in user-provider communications where the user was receptive, etc.); and/or any other suitable type of reinforcement learning models. However, applying machine learning communication models can be performed in any suitable manner.

In another variation, different communication models (e.g., generated with different algorithms, with different sets of features, with different input and/or output types, etc.) can be generated (and/or selected, retrieved, and/or executed) based on any one or more of the criteria described above in relation to the different bases for determining communication plans. For example, different communication models can be applied in relation to different data types (e.g., determining a communication schedule with a first communication model based on a care provider dataset; determining an automated communication content component with a second communication model based on a log of user dataset; etc.). Applying a plurality of communication models suited to different contexts can confer improvements to the processing system by improving personalization of a communication plan to a user (e.g., by tailoring to a user and/or care provider's unique behaviors), user outcomes, user conditions, retrieval speed for retrieving an appropriate communication model from a database (e.g., by associating communication model identifiers with particular user identifiers, care provider identifiers, and/or other identifiers), training and/or execution of communication models (e.g., through applying feature engineering rules for generating and/or selecting communication-related features most correlated with goals described above), and/or other suitable aspects of the processing system. However, applying any number of communication models can be performed in any suitable manner.

In relation to Block S150, as shown in FIG. 4, any number of communication plans can be determined based on any number of communications associated with any number of users and/or care providers. For example, Block S150 can include: determining a first tailored communication plan for a first user based on a user-provider communication between the first user and the care provider during a first time period; and determining a second tailored communication plan for the second user based on the user-provider communication, other aspects of the tailored communication plan, and/or other suitable data. Determining a communication plan is preferably performed by a communication determination system, but can additionally or alternatively be performed by a care provider, a treatment system, a mobile device, a supplemental device, and/or any other suitable component. For example, Block S150 can include generating a base communication plan for a user with the communication determination system; receiving care provider inputs on the base communication plan (e.g., comments, user insights, electronic health records associated with user conditions, etc.); and developing a modified communication plan based on the care provider inputs. Determining communication plans and/or associated communication collaboratively with a communication determination system and a care provider can aid in decreasing response times for care provider communications to users (e.g., where the care provider is interfacing with a plurality of users), reducing associated costs, enabling more care provider time to perform other functions, improving care provider engagement, and/or facilitating other suitable benefits.

Regarding Block S150, determining a communication plan and/or associated components can be performed prior to engaging a user (e.g., determining an engagement communication), during communications with a user (e.g., determining automated response communications to user responses; determining automated communications based on user cognitive state detected from analyzing datasets from Blocks S110-S145; etc.), after communications with a user (e.g., determining communication plans based on historic communications), in temporal relation (e.g., in response to) to transition events, emergency events, other trigger events, and/or at any suitable time and frequency. In a variation, Block S150 can include determining a user eligibility metric indicating suitability for receiving an automated communication, which can be based on user openness to communication (e.g., based on time of day, location, digital communication behavior trends, historical responses to automated communications, etc.), contextual parameters (e.g., likelihood of an automated communication serving a current user need, based on classifying user inputs such as survey responses into categories of user need, such as a psychological stress categories), user condition (e.g., increasing frequency of automated voice-communications over automated textual-communications based on identification of communication-related user conditions inhibiting user ability to communicate through text), and/or any other suitable data (e.g., described in relation to Blocks S110-S145, etc.). For example, Block S150 can include determining a user eligibility metric based on survey responses to a digitally-provided survey; and in response to the user eligibility metric exceeding a threshold (e.g., determining that a user is stressed based on the survey responses, and calculating that a breathing exercise delivered through automated communications can help with the stress), determining and transmitting automated communications to the user. Additionally or alternatively, determining user eligibility metrics can be performed in any suitable manner. However, determining communication plans S150 can be performed in any suitable manner.

3.7 Method—Transmitting an Automated Communication.

Block S160 recites: transmitting, based on the communication plan, a communication to the user at the mobile device. Block S160 functions to provide one or more communications to a user based on a communication plan determined in Block S150. Transmitting the communication to the user preferably includes transmitting an automated communication (e.g., generated, partially or fully, by the communication determination system), but any suitable communication can be transmitted. Transmitting communications can be performed according to a communication schedule, and/or can be performed in temporal relation trigger events including one or more of: care provider unavailability, user parameters (e.g., severity of user condition; user eligibility metric indicating openness to talk to a care provider; etc.), communication determination service availability (e.g., in relation to technical issues), emergency events, transition events, and/or other suitable trigger events. Additionally or alternatively transmitting communications can be performed in any manner analogous to U.S. application Ser. No. 15/005,923 entitled "Method for Providing Therapy to an Individual" and filed on 25 Jan. 2016, which is incorporated in its entirety by this reference, and/or in any suitable manner.

3.8 Method—Promoting a Therapeutic Intervention

Figure 7:
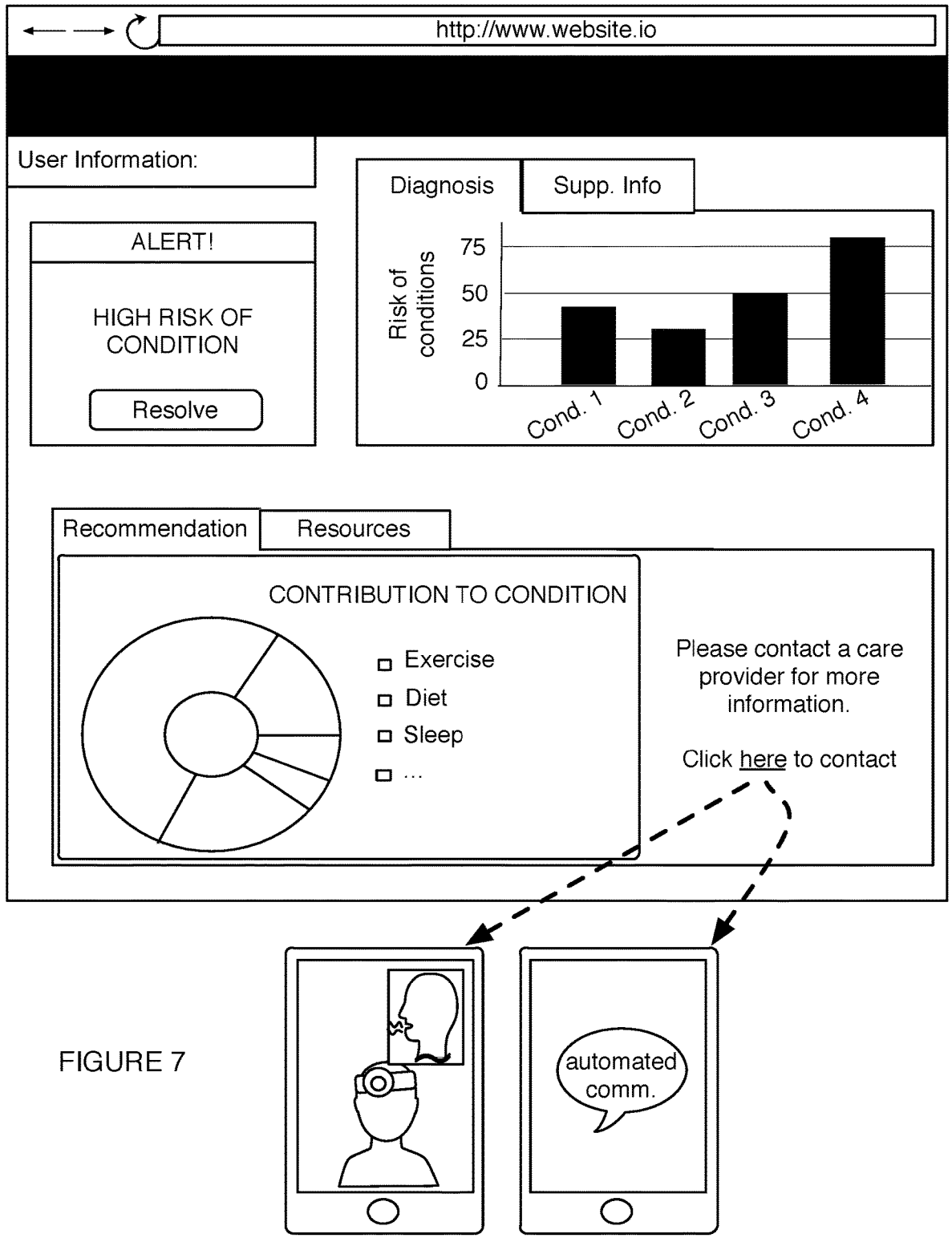
FIG. 7 is a schematic representation of an example of a therapeutic intervention.

Block S170 recites: promoting a therapeutic intervention to the user in association with transmitting a communication. Block S170 functions to leverage communications associated with the communication plan in facilitating promotion of one or more therapeutic interventions for improving a user condition. Therapeutic interventions can include any one or more of: health-related notifications (e.g., health tips provided through automated communications, etc.); therapy interventions (e.g., cognitive behavioral therapy exercises; etc.); care provider-related interventions (e.g., telemedicine, as shown in FIG. 7; scheduling care provider appointments; etc.); physical interventions (e.g., breathing exercises; meditation exercises; acupuncture; hypnosis; brain stimulation such as through magnetic pulses and/or electrical stimulation; etc.); dietary interventions; medication interventions; auditory interventions (e.g., controlling the mobile device to emit music samples in accordance with music therapy; controlling a personal assistance device to vocally emit content components of automated communications, such as with a tone determined based on a format component; etc.); mobile device and/or supplementary medical device interventions (e.g., modifying device operation parameters; etc.); ambient environment interventions (e.g., modification of light parameters, air quality and/or composition parameters, temperature parameters, humidity parameters; etc.) and/or any other suitable types of interventions. For example, the method 100 can include: automatically initiating a visual telemedicine communication (e.g., a type of user-provider communication) through a wireless communicable link between a mobile device associated with a user and a care provider device associated with the care provider; and updating the tailored communication plan based on the visual telemedicine communication and/or other suitable datasets (e.g., log of use dataset, mobility supplementary dataset, etc.). In another example, the method 100 can include: generating control instructions for operating a supplemental medical device; and activating the supplemental medical device based on transmitting the control instructions to the supplemental medical device.

Figure 6:
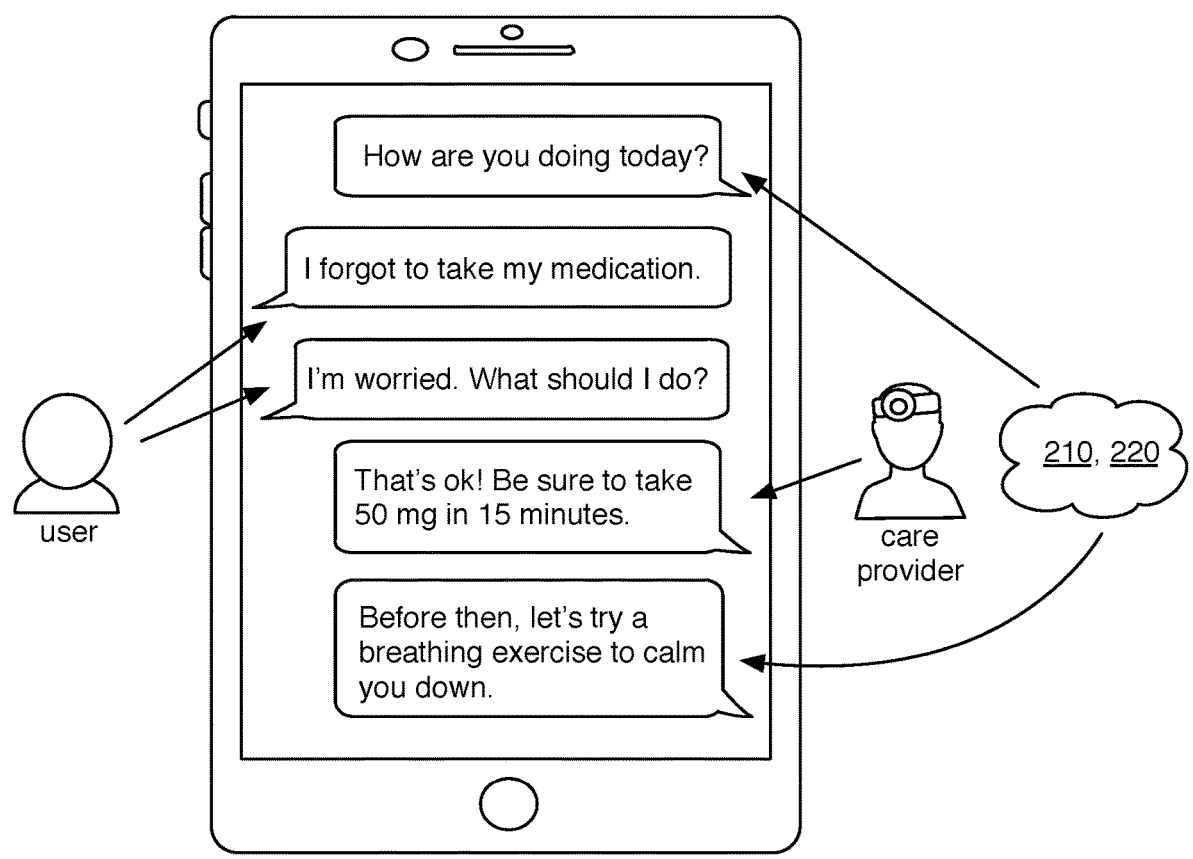
FIG. 6 is a schematic representation of an example of automated communication.

Regarding Block S170, promoting the therapeutic intervention is preferably performed in association with transmitting a communication, where the association can include one or more of: a temporal association such as performing the processes in serial and/or in parallel; a mobility-related association, such as performing the processes when the user is at the same target geographical location; a content-related and/or purpose-related association such as providing a therapeutic intervention and a communication pertaining to the same topic and/or operable to improve the same user condition; a care provider association, such as where the same care provider transmits the communication and promotes the therapeutic intervention; and/or any suitable type of associations. In a variation, Block S170 can include promoting a therapeutic intervention in the form of automated communications. For example, as shown in FIG. 6, Block S170 can include promoting a breathing exercise through step-by-step automated communications guiding a user through the breathing exercise. In another example, Block S170 can include promoting a guided meditation through generating automated communications describing exercises for the guided meditation; and generating control instructions for operating a personal assistance device to emit audio based on the automated communications (e.g., with a pitch associated with a gender of a care provider matched to the user). In another example, Block S170 can include promoting interactive therapy sessions through automated communications, such as including communications for one or more of: guiding discovery of thinking patterns (e.g., negative thinking); cognitive reframing (e.g., converting negative thoughts to positive thoughts); reminding users to perform therapeutic actions and/or associated skill-building (e.g., based on communication schedules predicted to optimize user outcomes; at predetermined time intervals; in response to manual care provider requests to transmit automated communications; etc.); and/or other suitable processes. In another example, Block S170 can include promoting automated communications operable to improve user communication behaviors (e.g., using automated communications to guide one or more users through learning about and applying alternative forms of communication, such as forms of communication that can substitute for criticism, contempt, defensiveness, withdrawal, and/or any other suitable communication forms, etc.).

In another variation, Block S170 can include promoting a therapeutic intervention in association with transmitting an automated communication including contextual information associated with the therapeutic intervention. In an example, Block S110 can include transmitting an automated reminder communication for performing an action associated with the therapeutic intervention (e.g., consuming medication; collecting sensor measurements associated with the user condition; performing a physical activity; etc.). In another example, Block S170 can include promoting a therapeutic intervention in association with transmitting automated educational communications including educational information on the therapeutic intervention (e.g., outcomes, side effects, instructions, etc.). In another example, Block Silo can include promoting a therapeutic intervention in association with automated communications related to user goals (e.g., reminders associated with goals established by a user and/or care provider; education associated with goals; etc.).

In relation to Block S170, promoting the therapeutic intervention in association with a communication can be based on any suitable criteria described in relation to determining a communication plan S150. For example, Block S160 can include scheduling promotion of a therapy based on a communication schedule of a communication plan. For example, the method 100 can include: determining a communication schedule for transmitting the automated communication; and coordinating the first schedule with a second schedule for promoting the therapeutic intervention. In another example, coordinating a communication schedule with a therapeutic intervention schedule can include defining a threshold time period; and promoting the therapeutic intervention and transmitting the automated communication within the threshold time period. In another example, determining a therapeutic intervention schedule can be based on a care provider availability schedule (e.g., scheduling promotion of a therapeutic intervention at a time overlapping with care provider availability, in order to schedule a care provider communication with the user within a threshold time period of promotion of the therapeutic intervention, etc.). In another example, promoting a therapeutic intervention can be performed in association with detecting an emergency event based on a transmitted communication (e.g., directing the user to emergency professionals and/or other associated users such as family in response to detecting a suicidal behavior from communications). Promoting therapeutic interventions can additionally or alternatively be analogous to approaches described in U.S. application Ser. No. 15/265,454 entitled "Method for Providing Health Therapeutic Interventions to a User" and filed on 14 Sep. 2016, which is incorporated in its entirety by this reference, and/or in any suitable manner.

3.9 Method—Updating a Communication Plan.

As shown in FIG. 5, the method 100 can additionally or alternatively include Block S180, which recites: updating the communication plan for the user based on at least one of a log of use dataset and a mobility supplementary dataset. Block S180 functions to update one or more components of the communication plan (and/or associated therapeutic interventions) based on one or more datasets described in Block S110-S145. Updating a communication plan can be performed in a manner analogous to or different from determining the communication plan (e.g., using different communication models to determine an initial communication plan, and to update the initial communication plan over time, etc.). In an example, the method 100 can include: determining a tailored communication plan for a user based on a first log of use dataset and a first mobility supplementary dataset; transmitting a automated communication during a second time period, based on the tailored communication plan; receiving a second log of use (e.g., including a user response to the automated communication; a user-provider communication transpiring subsequent to the automated communication; etc.) and a second mobility supplementary dataset associated with the second time period; and updating the tailored communication plan based on the second log of use and the second mobility supplementary dataset.

In a variation of Block S180, as shown in FIG. 5, updating the communication plan can include updating the target geographical location associated with one or more of: communication provision, therapeutic intervention promotion, transition events (e.g., notifying a care provider to control communications with the user, as opposed to automated communications, in response to a user at the target geographical location, such as a location associated with suicidal behavior), other trigger events, and/or any other suitable components. In an example, the method 100 can include: extracting a first location associated with the first log of use dataset from the first mobility supplementary dataset; determining, based on the first location, a communication schedule including a target geographical location for transmitting an automated communication; extracting a second location associated with the a second log of use dataset (e.g., including a user-provider communication) from a second mobility supplementary dataset; updating the target geographical location based on the second location; and transmitting the automated communication to the mobile device at the updated target geographical location. In another example, the method 100 can additionally or alternatively include scheduling a target geographical location for promoting a therapeutic intervention for improving the user condition; updating the target geographical location for promoting the therapeutic intervention (e.g., based on at least one dataset described in Block S110-S140); and promoting the therapeutic intervention at the target geographical location in association with transmitting the an automated communication.

In another variation of Block S180, as shown in FIG. 5, updating the communication plan can include updating a scheduled therapeutic intervention. For example, Block S180 can include: promoting a therapeutic intervention in association with a communication plan; receiving a log of use dataset and a mobility supplementary dataset associated with user response to the therapeutic intervention; and updating a scheduled therapeutic intervention (e.g., type of therapeutic intervention; manner of promoting the therapeutic intervention; etc.) based on the log of use dataset and the mobility supplementary dataset. In a specific example, Block S180 can include increasing frequency of outdoors-related therapeutic interventions associated with the communication plan based on survey responses to surveys administered through automated communications, where the survey responses indicate improved user outcomes from outdoors-related therapeutic interventions.

In another variation of Block S180, updating the communication plan can include updating content components and/or format components of a communication plan. In an example, the method 100 can include: determining a care provider digital communication behavior (e.g., frequent use of exclamation points, emojis, etc.) based on a user-provider communication, and updating a format component of a scheduled automated communication based on the care provider digital communication behavior (e.g., including exclamation points and emojis in the automated communication). In another example, Block S180 can include updating a format component for expressing the same content component. In a specific example, the method 100 can include: transmitting a first automated communication including a content component and a first format component; and determining a second automated communication including the content component and a second format component (e.g., based on a user response to the first automated communication; independent of a user response to the first automated communication; etc.), where the second format component is distinct from the first format component. However, any suitable components of a communication plan can be updated based on any suitable data (e.g., weighting features extracted from recent user-provider communications more heavily than features extracted from older user-provider communications, etc.). Regarding Block S180, updating the communication plan can be performed at any suitable time in relation to communications associated with a user (e.g., extracting features from communications in real-time to update the communication plan in real-time during the time period associated with the communications; updating the communication plan after time periods associated with communications; etc.), and/or at any suitable time and frequency. However, updating communication plans S180 can be performed in any suitable manner.

3.10 Method—Determining a Subgroup

The method 100 can additionally or alternatively include Block S190, which recites: determining one or more subgroups (e.g., user subgroup, care prouder subgroup). Block S190 functions to group one or more users and/or care providers based on shared characteristics (e.g., similar user parameters, care provider parameters, digital communication behaviors, mobility behaviors, device event behaviors, survey responses, etc.), in order to facilitate determination of a communication plan and/or other suitable portions of the method 100. In an example, Block S190 can include assigning a user and/or care provider to a user-provider relationship subgroup (e.g., sharing similar user digital communication behaviors in relation to communications with care providers; sharing similar user sentiment towards care provider and/or user-provider communications; grouping all users matched to a particular care provider and/or subset of care providers, etc.). In a specific example, Block S190 can include assigning a user to a user-provider relationship subgroup of a set of user-provider relationship subgroups, based on the set of mobility-communication features, such as where the user-provider relationship subgroup shares a digital communication behavior, and/or where the communication model is tailored to the user-provider relationship subgroup to improve personalization of a tailored communication plan for the user. However, determining and/or leveraging user subgroups can be performed in any suitable manner analogous to U.S. application Ser. No. 13/969,339, entitled "Method for Modeling Behavior and Health Changes" and filed on 16 Aug. 2013, and/or in any suitable manner.

4. System.

Figure 3:
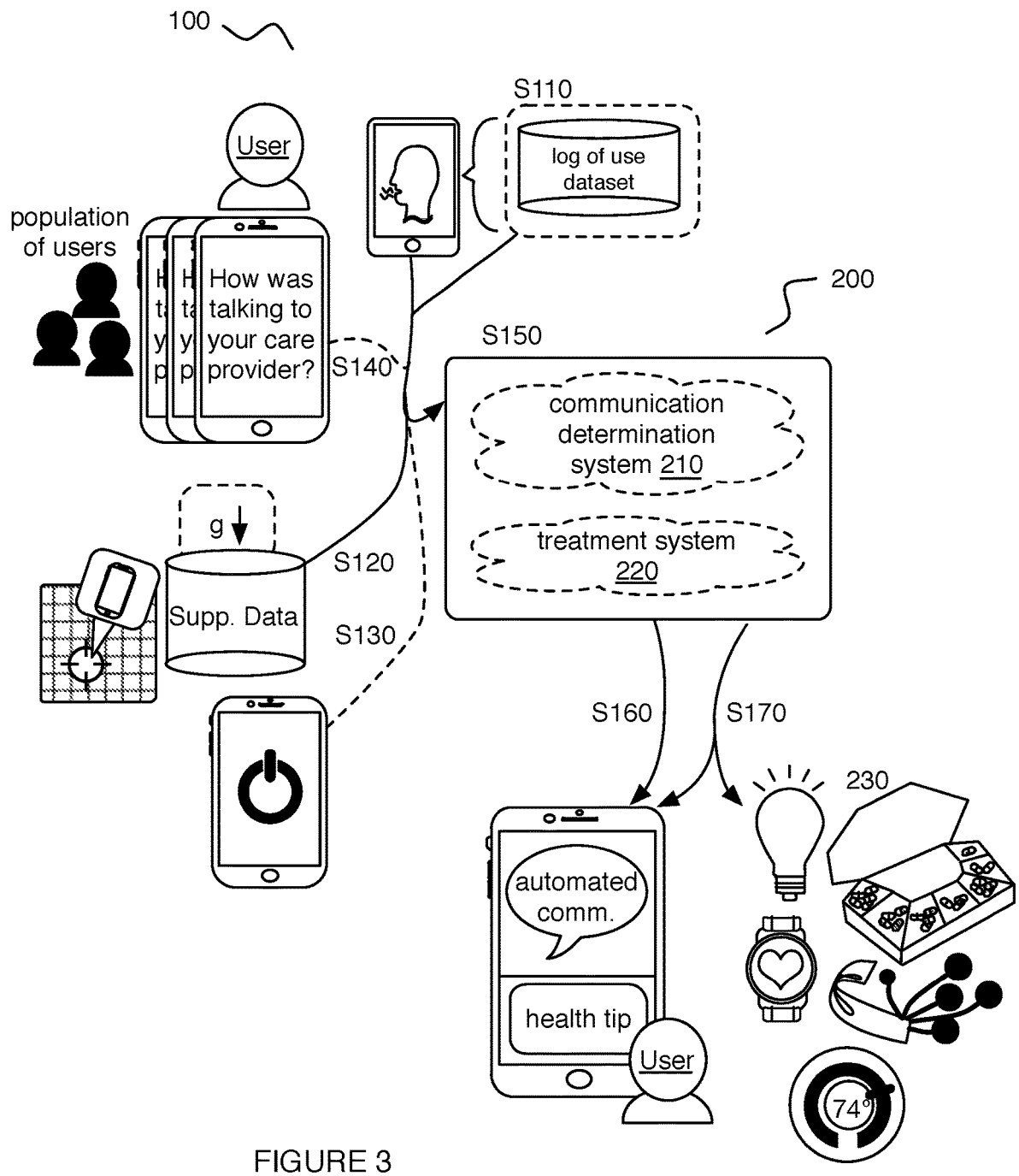
FIG. 3 is a schematic representation of embodiments of a method and system.

As shown in FIG. 3, embodiments of a system 200 for promoting user treatment through tailored communication with a user can include: a communication determination system 210 operable to perform Blocks S110-S160 and/or other portions of the method 100; and a treatment system 220 operable to automatically promote a treatment to the user in association with a communication transmitted according to a communication plan (e.g., such as in Block S160). The communication determination system 210 and/or treatment system 220 can include a processing system, an interface including a communication data aggregation module executing on a mobile device of the user; and/or any other suitable components operable to perform any suitable portions of the method 100. The system 200 can additionally or alternatively include a supplemental device 230 (e.g., a supplemental medical device, a supplemental personal assistant device, etc.) and/or any other suitable components. The system 200 and/or components of the system 200 (e.g., communication determination system 210, treatment system 220, etc.) can entirely or partially be executed by, hosted on, communicate with, and/or otherwise include: a remote computing system (e.g., a server, at least one networked computing system, stateless, stateful), a local computing system, a mobile device, a care provider device, databases, and/or by any suitable component. While the components of the system 200 are generally described as distinct components, they can be physically and/or logically integrated in any manner. For example, a remote computing system can implement functionality associated with both the communication determination system 210 and treatment system 220. In another example, functionality can be shared between the communication determination system 210, the treatment system 220, and/or any other suitable components of the system 200. However, the system 200 and associated components can be configured in any manner analogous to U.S. application Ser. No. 13/969,339 entitled "Method for Modeling Behavior and Health Changes" and filed on 16 Aug. 2013, U.S. application Ser. No. 15/265,454 entitled "Method for Providing Health Therapeutic Interventions to a User" and filed on 14 Sep. 2016, and U.S. application Ser. No. 15/245, 571 entitled "Method and System for Modeling Behavior and Heart Disease State" and filed on 24 Aug. 2016, each of which are herein incorporated in their entirety by this reference, and/or can be configured in any suitable manner.

The communication determination system 210 functions to collect and process datasets (e.g., described in Blocks S110-S145) in determining and/or executing communication plans for a user. The communication determination system 210 is preferably adherent to health-related privacy laws (e.g., HIPAA), and is preferably configured to privatize and/or anonymize data (e.g., communications) according to encryption protocols. For example, private health-related data (e.g., communications and/or associated data) can be stored temporarily on the user's mobile device in a locked and encrypted file folder on integrated or removable memory. Additionally or alternatively, the communication determination system 210 can comply with any suitable regulations. The communication determination system 210 is preferably operable to modify communication plans. For example, the communication determination system 210 can be operable to modify a visually perceptible digital element of a set of visually perceptible digital elements (e.g., corresponding to an automated communication; to a care provider communication) to improve display of the communication (e.g., at a mobile device for facilitating improvement of a condition of the user by a therapeutic intervention). However, the communication determination system 210 can be configured in any suitable manner.

The treatment system 220 functions to promote one or more therapeutic interventions in association with one or more communications. The treatment system 220 can include any one or more of supplementary medical devices 230 (e.g., ambient environment devices such as sensing and control systems for temperature, light, air quality and/or composition, humidity; biometric devices such as cardiovascular, EEG, EOG, EMG, ECG; medication devices such as automatic medication dispensers; personal assistant devices; etc.), mobile devices (e.g., mobile communication devices from which a log of use dataset is collected; user devices; care provider devices; etc.), and/or any other suitable devices. In an example, the therapeutic intervention can include an audio-based treatment operable to improve a user condition, and the treatment system 220 can include a speaker operable to emit the audio-based treatment based on an automated communication (e.g., a content component of the automated communication). In a specific example, the treatment system 220 can be operable to: obtain a set of computer-implemented rules that define the audio-based treatment as a function of a log of use data and a mobility supplementary data; and generate the audio-based treatment based on evaluating the log of use data and the mobility supplementary data against the set of computer-implemented rules. In another example, the therapeutic intervention can include a visual-based treatment (e.g., guided video exercise for meditation, breathing, etc.) presentable at a visual interface (e.g., of the treatment system; of another device; based on the automated communication and/or other suitable data; smart windows; smart mirrors; etc.). However, the treatment system 220 can be configured in any suitable manner.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a computer or mobile device 209, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions. The embodiments include every combination and permutation of the various system components and the various method processes, including any variations, examples, and specific examples. As a person skilled in the art will recognize from the previous detailed description and from the figures and claims, modifications and changes can be made to the embodiments of the invention without departing from the scope of this invention as defined in the following claims.

We claim:

1. A system for promoting user treatment through tailored communication with a user, the system comprising:
   a communication determination system, wherein the communication system:
      receives log of use data associated with user digital communication behavior at a mobile device, the log of use data further associated with a care professional communication between the user and a care professional;
      receives mobility supplementary data associated with a mobility-related sensor of the mobile device, the mobility supplementary data further associated with the care professional communication;
      assigns the user to a user subgroup of a set of user subgroups based on at least one of the log of use data and the mobility supplementary data;
      retrieves a tailored communication model based on the user subgroup;
      generates a tailored communication plan for the user based on the tailored communication model; and
      transmits an automated communication to the user at the mobile device according to the tailored communication plan; and
   a treatment system, wherein the treatment system automatically initiates provision of a treatment to the user in association with the automated communication.

2. The system of claim 1, wherein the treatment is an audio-based treatment operable to improve a condition of the user, and wherein the treatment system comprises a speaker operable to emit the audio-based treatment based on the automated communication.

3. The system of claim 2, wherein the treatment system further:
   obtains a set of computer-implemented rules that define the audio-based treatment as a function of the log of use data and the mobility supplementary data; and
   generates the audio-based treatment based on evaluating the log of use data and the mobility supplementary data against the set of computer-implemented rules.

4. The system of claim 1,
   wherein the tailored communication plan comprises a set of visually perceptible digital elements corresponding to the automated communication, and
   wherein the communication determination system further modifies a visually perceptible digital element of the set of visually perceptible digital elements to improve display of the automated communication at the mobile device for facilitating improvement of a condition of the user by the treatment.

5. The system of claim 1, wherein the treatment is a visual-based treatment operable to improve a condition of the user, and wherein the treatment system comprises a visual interface operable to present the visual-based treatment based on the automated communication.

6. A method for facilitating improvement of a user condition through communication tailored for a user-provider relationship between a user and a care provider, the method comprising:
receiving a log of use dataset associated with a digital communication behavior at a mobile device, the log of use dataset further associated with a user-provider communication between the user and the care provider;
receiving a mobility supplementary dataset corresponding to a mobility-related sensor of the mobile device, the mobility supplementary dataset associated with the user-provider communication;
extracting, from the log of use dataset and the mobility supplementary dataset, a set of mobility-communication features associated with the user-provider relationship based on a feature engineering computer-implemented rule operable to improve a communication model;
assigning the user to a user-provider relationship subgroup of a set of user-provider relationship subgroups, based on the set of mobility-communication features, wherein the user-provider relationship subgroup shares the digital communication behavior;
determining a tailored communication plan for the user based on the set of mobility-communication features and the communication model, wherein the communication model is tailored to the user-provider relationship subgroup to improve personalization of the tailored communication plan for the user; and
automatically initiating provision of a therapeutic intervention to the user in association with transmitting an automated communication according to the tailored communication plan.

7. The method of claim 6,
wherein extracting the set of mobility-communication features comprises generating a text messaging location feature based on associating a text messaging parameter from the log of use dataset with a location parameter from the mobility supplementary dataset, according to the feature engineering computer-implemented rule, and
wherein determining the tailored communication plan comprises determining the tailored communication plan based on the text messaging location feature.

8. The method of claim 6, wherein the text messaging location feature comprises at least one of:
a text messaging frequency, between the user and the care provider, at a location, and
a text messaging duration, between the user and the care provider, at the location.

9. The method of claim 6, wherein the determining the tailored communication plan comprises determining, based on the digital communication behavior associated with the user, an automated communication frequency for transmitting a set of automated communications comprising the automated communication to the user.

10. The method of claim 9, wherein determining the automated communication frequency comprises determining the automated communication frequency based on the user condition and the digital communication behavior.

11. The method of claim 6, wherein determining the tailored communication plan comprises determining a first schedule for transmitting the automated communication, and wherein promoting the therapeutic intervention comprises coordinating the first schedule with a second schedule for promoting the therapeutic intervention.

12. The method of claim 11, wherein coordinating the first schedule with the second schedule comprises defining a threshold time period, and wherein promoting the therapeutic intervention and transmitting the automated communication are performed within the threshold time period.

13. The method of claim 11, further comprising receiving a care provider availability schedule, wherein determining the first schedule comprises determining the first schedule based on the care provider availability schedule.

14. A method for facilitating improvement of a user condition through tailored communication with a first user, the method comprising:
receiving a first log of use dataset associated with user digital communication behavior at a first mobile device, the first log of use dataset further associated with a first time period;
receiving a first mobility supplementary dataset corresponding to a mobility-related sensor of the first mobile device, the first mobility supplementary dataset associated with the first time period;
assigning the user to a user subgroup of a set of user subgroups based on at least one of the first log of use dataset and the first mobility supplementary dataset;
retrieving a tailored communication model based on the user subgroup;
determining a first tailored communication plan for the first user based on the tailored communication model, wherein the first tailored communication plan is operable to facilitate improvement of the user condition;
transmitting, based on the first tailored communication plan, a first automated communication to the first user at the first mobile device during a second time period;
receiving a second log of use dataset associated with a first user-provider communication between the first user and a care provider during the second time period;
receiving a second mobility supplementary dataset corresponding to the mobility-related sensor and associated with the second time period;
updating the first tailored communication plan for the first user based on the second log of use dataset and the second mobility supplementary dataset; and
automatically initiating provision of a therapeutic intervention to the user based on the updated tailored communication plan.

15. The method of claim 14, further comprising:
determining a second tailored communication plan for a second user based on a second user-provider communication between the second user and the care provider during the second time period,
wherein updating the first tailored communication plan for the first user comprises updating the first tailored communication plan based on the second user-provider communication, the second log of use dataset, and the second mobility supplementary dataset.

16. The method of claim 15, further comprising:
automatically initiating a visual telemedicine communication comprising the second user-provider communication through a wireless communicable link between a second mobile device associated with the second user and a care provider device associated with the care provider, and
wherein updating the first tailored communication plan for the first user comprises updating the first tailored communication plan based on the visual telemedicine communication, the second log of use dataset, and the second mobility supplementary dataset.

17. The method of claim 14, further comprising:

extracting a first location associated with the first log of use dataset from the first mobility supplementary dataset, wherein determining the first tailored communication plan comprises determining, based on the first location, a target geographical location for transmitting a second automated communication; and extracting a second location associated with the first user-provider communication from the second mobility supplementary dataset, wherein updating the first tailored communication plan comprises updating the target geographical location based on the second location; and transmitting the second automated communication to the first mobile device at the target geographical location.

18. The method of claim 17, wherein determining the first tailored communication plan comprises scheduling the target geographical location for promoting a therapeutic intervention for improving the user condition, wherein updating the first tailored communication plan comprises updating the target geographical location for promoting the therapeutic intervention, and the method further comprising:

promoting the therapeutic intervention at the target geographical location in association with transmitting the second automated communication.

19. The method of claim 18, wherein determining the first tailored communication plan comprises determining the therapeutic intervention, and wherein updating the first tailored communication plan comprises updating the therapeutic intervention based on the second log of use dataset and the second mobility supplementary dataset.

20. The method of claim 14, wherein determining the first tailored communication plan comprises generating the first automated communication comprising a content component and a first format component, the method further comprising:

determining a care provider digital communication behavior based on the first user-provider communication, wherein updating the first tailored communication plan comprises generating a second automated communication comprising the content component and a second format component based on the care provider digital communication behavior, and wherein the second format component is distinct from the first format component.

* * * * *